(12) United States Patent
Bartkovitz et al.

(10) Patent No.: US 7,423,051 B2
(45) Date of Patent: Sep. 9, 2008

(54) 2,6-DIAMINOPYRIDINE DERIVATIVES

(75) Inventors: David Joseph Bartkovitz, Nutley, NJ (US); Xin-Jie Chu, Livingston, NJ (US); Allen John Lovey, North Caldwell, NJ (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 622 days.

(21) Appl. No.: 11/165,912

(22) Filed: Jun. 24, 2005

(65) Prior Publication Data

US 2006/0014708 A1     Jan. 19, 2006

Related U.S. Application Data

(60) Provisional application No. 60/588,122, filed on Jul. 15, 2004.

(51) Int. Cl.
*A61K 31/4545*  (2006.01)
*C07D 401/12*  (2006.01)

(52) U.S. Cl. ............ 514/318; 546/194; 546/268.1; 514/336

(58) Field of Classification Search .......... 514/318, 514/336; 546/194, 268.1
See application file for complete search history.

(56) References Cited

U.S. PATENT DOCUMENTS

| | | | |
|---|---|---|---|
| 6,262,096 | B1 | 7/2001 | Kim et al. |
| 2003/0220326 | A1 | 11/2003 | Chong et al. |

FOREIGN PATENT DOCUMENTS

| | | |
|---|---|---|
| WO | WO 99/21845 | 5/1999 |
| WO | WO 01/19825 | 3/2001 |
| WO | WO 01/38315 | 5/2001 |
| WO | WO 01/79198 | 10/2001 |
| WO | WO 2004/074283 A1 | 9/2004 |
| WO | WO 2005/051387 | 6/2005 |

OTHER PUBLICATIONS

V. Mesguiche, et al., Bioorganic & Medicinal Chemistry Letters, vol. 13, pp. 217-222 (2003), XP002356484.
Sielecki T., et al., J. Med. Chem., 2000, vol. 43, pp. 1-18.
Lin, R. et al., Bioorganic & Medicinal Chemistry Letters, 2005, vol. 15(9) pp. 2221-2224.
Lin, R. et al., Journal of Medicinal Chemistry Letters, 2005, pp. A-D.
Harris, W. & Wilkinson, S., Emerging Drugs, 2000, vol. 5, pp. 287-297.
Dumas, J., Exp. Opin. Ther. Patents, 2001, vol. 11, pp. 405-429.

*Primary Examiner*—Charanjit S Aulakh
(74) *Attorney, Agent, or Firm*—George W. Johnston; Patricia S. Rocha-Tramaloni

(57) ABSTRACT

Novel 2,6-diaminopyridine derivatives of formula

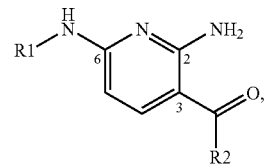

wherein $R^1$ and $R^2$ are as defined below, are disclosed. These compounds inhibit cyclin-dependent kinases. These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung, colon and prostate tumors. Also disclosed are intermediates useful in the preparation of these novel 2,6-diaminopyridine derivatives.

24 Claims, No Drawings

2,6-DIAMINOPYRIDINE DERIVATIVES

PRIORITY TO RELATED APPLICATIONS

This application claims the benefit of Provisional Application Ser. No. 60/588,122, filed Jul. 15, 2004, which is herein incorporated by reference.

FIELD OF THE INVENTION

The present invention relates to novel 2,6-diaminopyridine derivatives that inhibit cyclin-dependent kinases. These compounds and their pharmaceutically acceptable salts and esters have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors. Finally, this invention is also directed to novel intermediate compounds useful in the preparation of the novel diaminopyridines herein disclosed.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The four primary phases of cell cycle control are generally describes as $G_1$, S, $G_2$, and M. Some essential enzymes for cell cycle control appear to be cyclin D/Cdk4, cyclin D/Cdk6, cyclin E/Cdk2, cyclin A/Cdk2, and cyclin B/Cdk1 (also known as Cdc2/cyclin B). Cyclin D/Cdk4, cyclin D/Cdk6, and cyclin E/Cdk2 control passage through the $G_1$-phase and the $G_1$- to S-phase transition by phosphorylation of the retinoblastoma phosphoprotein, pRb. Cyclin A/Cdk2 regulates passage through the S-phase, and cyclin B/Cdk1 controls the $G_2$ checkpoint and regulates entry into M (mitosis) phase.

The cell cycle progression is regulated by Cdk1 (cdc2) and Cdk2 beyond early $G_1$ when cells are committed to cytokinesis. Therefore, drug inhibition of these Cdks is likely not only to arrest cell proliferation, but also to trigger apoptotic cell death. Once the cells pass the $G_1$ restriction point and are committed to S phase, they become independent of growth factor stimulation for continued cell cycle progression.

Following completion of DNA replication, cells enter the $G_2$ phase of the cell cycle in preparation for M phase and cytokinesis. Cdk1 has been shown to regulate passage of cells through these later phases of the cell cycle in association with both cyclins A and B. Complete activation of Cdk1 requires both cyclin binding and specific phosphorylation (Morgan, D. O., De Bondt, H. L., Curr. Opin. Cell. Biol. 1994, 6, 239-246). Once activated, Cdk1/cyclin complexes prepare the cell for division during M phase.

The transition from $G_1$ phase into S phase as stated above is regulated by the complex of Cdk4 with cyclin D and Cdk2. with cyclin E. These complexes phosphorylate the tumor suppressor protein Retinoblastoma (pRb), releasing the transcription factor E2F and allowing the expression of genes required in S phase (Nevins, J. R. Science 1992, 258, 424- 429; Lavia, P. BioEssays 1999, 21, 221-230). Blocking the activity of the Cdk4/cyclin D and Cdk2/cyclin E complexes arrests the cell cycle in $G_1$ phase. For example, the proteins of the INK4 family, including $p16^{INK4a}$, which block the kinase activity of the Cdk4/cyclin D complex, cause arrest in $G_1$ (Sherr, C. J. Science 1996, 274, 1672-1677). The specific block has been reviewed (Vidal, A. Gene 2000, 247,1-15).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. J. Biol. Chem. 1999, 274, 13961-13969).

Numerous defects in the pRb pathway have been shown to be involved in various cancers. For example, overexpression of Cdk4 has been observed in cases of hereditary melanoma (Webster, K. R. Exp. Opin. Invest. Drugs 1998, 7, 865-887); cyclin D is overexpressed in many human cancers (Sherr, C. J. Science 1996, 274,1672-1677); p16 is mutated or deleted in many tumors (Webster, K. R. Exp. Opin. Invest. Drugs 1998, 7, 865-887); and pRb function is lost through mutation or deletion in many human cancers (Weinberg, R. A. Cell 1995, 81, 323-330). Defects in this pathway have also been shown to have an effect on prognosis. For example, loss of p16 is correlated with poor prognosis in non-small-cell lung carcinoma (NSCLC) and malignant melanoma (Tsihlias, J. et al. Annu. Rev. Med. 1999, 50, 401-423). Abnormalities of cyclin D1 and/or pRb at the gene and/or expression level were present in more than 90% of a series of non-small cell lung cancer specimens, indicating that cyclin D1 and/or pRb represent an important step in lung tumorigenesis (Marchetti, A. et al. Int. J. Cancer 1998, 75, 573-582). In 49 out of 50 pancreatic carcinomas (98%), the pRb/p16 pathway was abrogated exclusively through inactivation of the p16 gene and cyclin D connected (Schutte, M. et al. Cancer Res. 1998, 57, 3126-3134). For a review on the relation between expression of pRb and the cyclin/cyclin dependent kinases in a number of tissues see Teicher, B. A.. Cancer Chemother. Pharmacol. 2000, 46,293-304.

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of proteins involved in the pathway. See, e.g., Lukas, J. et al. Nature 1995, 79, 573-582; Nevins, J. R. Science 1992, 258, 424-429; Lim, I. K. et al. Molecular Carcinogenesis 1998, 23, 25-35; Tam, S. W. et al. Oncogene 1994, 9, 2663-2674; Driscoll, B. et al. Am. J. Physiol. 1997, 273 (Lung Cell. Mol. Physiol.), L941-L949; and Sang, J. et al. Chin. Sci. Bull. 1999, 44, 541-544).

The role of cdks in the regulation of cellular proliferation is thus well established. For example, as shown above, there is an extensive body of literature validating the use of compounds inhibiting targets in the Cdk4, Cdk2 and Cdk1 pathways as anti-proliferative therapeutic agents. Inhibitors of cellular proliferation thus act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, but not limited to herpervirus, poxvirus, Epstein- Barr virus), autoimmune disease (e.g. lupus, rheumatoid arthritis, psoriasis, inflammatory bowel disease), neurodegenerative disorders (including but not limited to Alzheimer's disease), and neurodegenerative diseases (e.g. Parkinson's disease, amyotrophic lateral sclerosis, retinitis pigmentosa, spinal muscular atrophy, and cerebral degeneration).

Several distinct classes of small molecules have been identified as inhibitors of Cdks: olomoucine and other purine analogs, flavopiridol, staurosporine, UCN-01 and other indolocarbazoles, 9-hydroxyellipticine, indirubin, paullones, diaryl ureas, quinazolines, indopyrazoles, [2,3-d]pyridopyrimidines, fascaplysin, aminothiazoles, diaminothiazoles, p-teridinones, and pyrazoles or example (Carlson et. al., Cancer Res.. 1996, 56, 2973-2978: De Azevedo et al., Eur. J. Biochem., 1997, 243, 518-526; Bridges, A. J., Exp. Opin. Ther. Patents. 1995, 5, 12451257; Reinhold et al., J. Biol. Chem. 1998, 278, 3803-3807; Kakeya, H. et. al., Cancer Res.. 1998, 58, 704-710; Harper, J. W., Cancer Surveys 1997, 29, 91-107; Harrington, E. A., et al., Proc. Natl. Acad. Sci. USA 1998, 95,11945-11950; Meijer, L., et al., Eur. J. Biochem.. 2000, 267, 1-13; Garrett, M. D. et. al., Current Opin. Genetics Develop. 1999, 9, 104-111; Mgbonyebi, O. P. et al., Cancer Res.. 1999, 59, 1903-1910; Hoessel et al., Nature Cell Biology. 1999, 1, 60-67; Zaherevitz et al., Cancer Res., 1999, 59, 2566-2569; Honma, T., et al., $221^{St}$ National ACS Meeting.. 2001: Medi 136; Sielecki, T. M., et al., Bioorg. Med. Chem. Lett. 2001, 11,1157-1160; Nugiel, D. A., et al., J. Med. Chem., 2001, 44,1334-1336; Fry, D. W. et al., J. Biol. Chem. 2001, 276, 16617-15523; Soni, R., et al., Biochem. Biophys. Res. Commun. 2000, 275, 877; Ryu, C-K. et al., Bioorg. Med. Chem. Lett., 2000, 10, 461; Jeong, H-W., et al., Bioorg. Med. Chem. Lett. 2000, 10, 1819; Toogood et al., J. Med. Chem., 2000, 43, 4606-4616; Chong, W., Fischer, Curr. Opin. in Drug Discov. and Develop., 2001, 4, 623-634, WO0009921845, Toogood. P., WO01 19825, Toogood P., WO0138315, Reich S. H., WO0179198, Webster, K. U.S. Pat. No. 6,262,096.

For reviews of compounds inhibiting the Cdk4/cyclin D pathway see: Harris, W. and Wilkinson, S., Emerging Drugs.. 2000, 5, 287-297; Dumas, J., Exp. Opin. Ther. Patents. 2001, 11, 405-429; Sielecki T., et. al., J. Med. Chem.. 2000, 43, 1-18.

SUMMARY OF THE INVENTION

The present invention relates to novel diaminopyridines of the formula

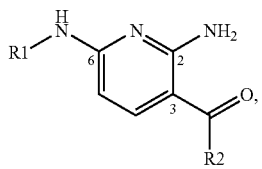

I wherein $R^1$ is selected from the group
heterocycle and lower alkyl-heterocycle, wherein the heterocycle moiety in both instances optionally may be substituted by up to four substituents independently selected from
H,
lower alkyl,
lower alkyl substituted by oxo, $OR^{12}$, $CO_2R^{12}$, $NR^5R^6$, $S(O)NR^{15}$, aryl or $C(O)NR^5R^6$,
$CO_2R^7$,
$COR^{12}$,
$C(O)NR^{13}R^{14}$,
$S(O)NR^{15}$,
oxo,
$OR^{12}$; or
$NR^5R^6$, $R^2$ is selected from the group
aryl, heteroaryl, cycloalkyl and heterocycle, wherein each may be substituted by up to four substituents independently selected from the group
lower alkyl,
lower alkyl substituted by halogen or $OR^{10}$,
halogen,
$OR^{12}$,
$NO_2$,
CN,
$NR^5R^6$,
$S(O)_n$—$R^9$, and
$SO_2$—$NR^{16}R^{17}$;

$R^5$ and $R^6$ are each independently selected from the group
H,
lower alkyl,
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^{13}R^{14}$, $C(O)NR^{13}R^{14}$ or $SO_2R^{15}$,
aryl,
aryl substituted by $NR^{13}R^{14}$, $OR^{12}$, $CO_2R^{12}$, $C(O)NR^{13}R^{14}$, $SO_2R^{15}$, halogen, lower alkyl, or lower alkyl substituted by halogen, $OR^{12}$, oxo, $CO_2R^{12}$, $C(O)NR^{13}R^{14}$ or $NR^{13}R^{14}$,
$SO_2R^{15}$,
$CO_2R^{12}$,
$COR^{12}$, and

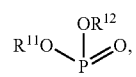

or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^{13}R^{14}$, lower alkyl and lower alkyl substituted by $OR^{12}$;

$R^7$ is selected from the group
H,
lower alkyl,
lower alkyl substituted by $OR^{12}$, $CO_2R^{12}$, $NR^5R^6$, or $C(O)NR^5R^6$,
halogen,
oxo,
aryl,
aryl substituted by up to three substituents independently selected from lower alkyl, halogen and $NR^5R^6$,
cycloalkyl,
cycloalkyl substituted by OH, oxo, or $NH_2$,
$SO_2R^{15}$, and
$COR^{12}$;

$R^9$ is selected from the group
  H, and
  lower alkyl;

$R^{10}$ is selected from the group
  lower alkyl,
  aryl, and
  aryl substituted by halogen or $NR^5R^6$;

$R^{11}$ is selected from the group
  H,
  lower alkyl, and
  lower alkyl substituted by oxo and halogen;

$R^{12}$ is selected from the group
  H,
  lower alkyl, and
  lower alkyl substituted by $NR^5R^6$ or $OR^{11}$;

$R^{13}$ and $R^{14}$ are each independently selected from the group
  H,
  lower alkyl,
  lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
  cycloalkyl,
  cycloalkyl substituted by $CO_2R^{12}$, $OR^{12}$, $NR^5R^6$, $CONR^5R^6$ or $SO_2R^{15}$,
  aryl,
  aryl substituted by $NR^5R^6$, $OR^{12}$, $CO_2R^{12}$, $CONR^5R^6$, $SO_2R^{15}$, halogen, lower alkyl, and lower alkyl substituted by halogen, $OR^{12}$, oxo, $CO_2R^{12}$, $C(O)NR^5R^6$ or $NR^5R^6$;
    $SO_2R^{15}$,
    $CO_2R^{12}$,
    $COR^{12}$, and

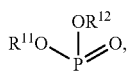

or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group
  aryl,
  aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
  heteroaryl,
  heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
    $NR^5R^6$,
    lower alkyl,
    lower alkyl substituted by halogen, $OR^{12}$, oxo, $CO_2R^{12}$, $C(O)NR^5R^6$ or $NR^5R^6$,
  heterocycle, and
  heterocycle substituted by the group $CO_2R^{12}$, $COR^{12}$, $SO_2R^{12}$, lower alkyl, $C(O)NR^5R^6$ or $NR^5R^6$;

$R^{16}$ and $R^{17}$ are each independently selected from the group
  H, and
  lower alkyl, or, alternatively, the group —$NR^{16}R^{17}$ can form a ring having a total of from 3 to 7 ring atoms, said ring atoms comprising in addition to the nitrogen to which $R^{16}$ and $R^{17}$ are bonded, carbon ring atoms, said carbon ring atoms optionally being replaced by one or more additional N or O ring atoms, and said ring atoms optionally being substituted by lower alkyl, OH, oxo and $NH_2$; and
  n is 0, 1 or 2;

or the pharmaceutically acceptable salts or esters thereof.

These compounds inhibit cyclin-dependent kinases. These compounds and their pharmaceutically acceptable salts and esters have antiproliferative activity and are useful in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically acceptable salt or ester thereof.

Finally, this invention also relates to novel intermediate compounds useful in the preparation of a compound of formula I.

DETAILED DESCRIPTION OF THE INVENTION

Definitions

As used herein, the following terms shall have the following definitions.

"Aryl" means a monovalent, monocyclic or bicyclic, aromatic carbocyclic hydrocarbon radical, preferably a 6-10 membered aromatic aromatic ring system. Preferred aryl groups include, but are not limited to, phenyl, naphthyl, tolyl and xylyl.

"Carbonyl" means the radical C=O.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably fluorine or chlorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole, benzofuran and tetrazolyl.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, S(O)n (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$K_i$" refers to a measure of the thermodynamic binding of the ligand/inhibitor (that is, a compound according to the invention) to the target protein. $K_i$ can be measured, inter alia, as is described in Example 53, infra.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Oxo" means =O.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids ($R^{40}C(=O)OH$) are lower alkyl esters which may be substituted with $NR^{41}R^{42}$ where $R^{41}$ and $R^{42}$ are lower alkyl, or where $NR^{41}R^{42}$ taken together form a monocyclic aliphatic heterocycle, such as pyrrolidine, piperidine, morpholine, N-methylpiperazine, etc.; acyloxyalkyl esters of the formula $R^{40}C(=O)OCHR^{43}OC(=O)R^{44}$ where $R^{43}$ is hydrogen or methyl, and $R^{44}$ is lower alkyl or cycloalkyl; carbonate esters of the formula $R^{40}C(=O)OCHR^{43}OC(=O)OR^{45}$ where $R^{43}$ is hydrogen or methyl, and $R^{45}$ is lower alkyl or cycloalkyl; or aminocarbonylmethyl esters of the formula $R^{40}C(=O)OCH_2C(=O)NR^{41}R^{42}$ where $R^{41}$ and $R^{42}$ are hydrogen or lower alkyl, or where $NR^{41}R^{42}$ taken together form a monocyclic aliphatic heterocycle, such as pyrrolidine, piperidine, morpholine, N-methylpiperazine, etc. As used herein, R40 has the same definition as $R^1$.

Examples of lower alkyl esters are the methyl, ethyl, and n-propyl esters, and the like. Examples of lower alkyl esters substituted with $NR^{41}R^{42}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy) ethyl and 1-(cyclohexyloxycarbonyloxy)ethyl esters. Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp.108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp.196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the present invention relates to compounds of formula I

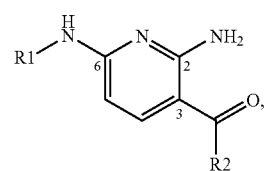

or the pharmaceutically acceptable salts or esters thereof, wherein $R^1$ and $R^2$ are as defined above.

In a preferred embodiment of the compounds of formula I, $R^2$ is phenyl, preferably phenyl substituted by halogen, most preferably F, $OR^{12}$ wherein $R^{12}$ is lower alkyl or lower alkyl. In a most preferred embodiment, $R^2$ is phenyl substituted by one or two F molecules and one $OR^{12}$ group wherein $R^{12}$ is lower alkyl, preferably methyl.

In another preferred embodiment of the compounds of formula I, $R^2$ is as defined above and $R^1$ is selected from the group

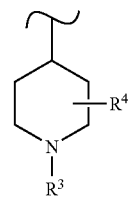
(a)

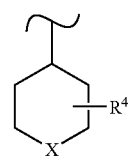
(b)

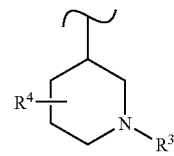
(c)

-continued (d)

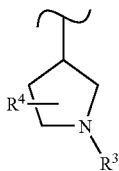

wherein
R³ is selected from the group
H,
lower alkyl,
lower alkyl substituted by oxo, OR¹², CO₂R¹², NR⁵R⁶, SO₂R¹⁵, aryl or C(O)NR⁵R⁶,
CO₂R⁷,
COR¹²,
C(O)NR⁵R⁶, and
SO₂R¹⁵;
R⁴ is selected from the group
H,
OR¹¹,
lower alkyl,
NR⁵R⁶,
NO₂,
oxo
CN, and
halogen;
R⁵ and R⁶ are each independently selected from the group
H,
lower alkyl,
lower alkyl substituted by oxo, CO₂R¹², OR¹², NR¹³R¹⁴, C(O)NR¹³R¹⁴, SO₂R¹⁵, NSO₂R¹², heteroaryl, heterocycle, or heterocycle substituted by oxo,
cycloalkyl,
cycloalkyl substituted by CO₂R¹², OR¹², NR¹³R¹⁴, C(O)NR¹³R¹⁴ or SO₂R¹⁵,
aryl,
aryl substituted by NR³R¹⁴, OR¹², CO₂R¹², CONR¹³R¹⁴, SO₂R¹⁵, halogen, lower alkyl, and lower alkyl substituted by halogen, OR , oxo, CO₂R¹², CONR¹³R¹⁴ or NR¹³R¹⁴;
SO₂R¹⁵,
CO₂R¹²,
COR¹², and

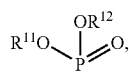

or alternatively, the group —NR⁵R⁶ can form a ring having a total of from 3 to 7 ring atoms, said ring atoms comprising in addition to the nitrogen to which R⁵ and R⁶ are bonded, carbon ring atoms, said carbon ring atoms optionally being replaced by one or more additional N or O ring atoms or the group SO₂, and said ring atoms optionally being substituted by OH, oxo, N¹³R¹⁴, lower alkyl and lower alkyl substituted by OR¹²;
R⁷ is selected from the group
H,
lower alkyl,
lower alkyl substituted by OR¹², CO₂R¹², NR⁵R⁶, or CONR⁵R⁶, halogen,
oxo,
aryl,
aryl substituted by up to three substituents independently selected from lower alkyl, halogen, or NR⁵R⁶,
cycloalkyl,
cycloalkyl substituted by OH, oxo, or NH₂,
SO₂R¹⁵, and
COR¹²;
R¹⁰ is selected from the group
lower alkyl,
aryl, and
aryl substituted by halogen or NR⁵R⁶;
R¹¹ is selected from the group
H,
lower alkyl, and
lower alkyl substituted by oxo and halogen;
R¹² is selected from the group
H
lower alkyl, and
lower alkyl substituted by halogen, oxo, NR⁵R⁶ or OR¹¹;
R¹³ and R¹⁴ are independently selected from
H,
lower alkyl,
lower alkyl substituted by CO₂R¹², OR¹², NR⁵R⁶, C(O)NR⁵R⁶, SO₂R¹⁵, NSO₂R¹², heteroaryl, heterocycle, or heterocycle substituted by oxo,
cycloalkyl,
cycloalkyl substituted by CO₂R¹², OR¹², NR⁵R⁶, C(O)NR⁵R⁶ or SO₂R¹⁵,
aryl,
aryl substituted by NR⁵R⁶, OR¹², CO₂R¹², C(O)NR⁵R⁶, SO₂R¹⁵, halogen, lower alkyl, and lower alkyl substituted by halogen, OR¹², oxo, CO₂R¹², C(O)NR⁵R⁶ and NR⁵R⁶;
SO₂R¹⁵,
CO₂R¹²,
COR¹², and

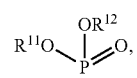

or alternatively, the group —NR¹³R¹⁴ can form a ring having a total of from 3 to 7 ring atoms, said ring atoms comprising in addition to the nitrogen to which R¹³ and R¹⁴ are bonded, carbon ring atoms, said carbon ring atoms optionally being replaced by one or more additional N or O ring atoms, and said ring atoms optionally being substituted by OH, oxo, NR⁵R⁶, lower alkyl and lower alkyl substituted by OR¹²;
R¹⁵ is selected from the group
aryl,
aryl substituted by the group halogen, CO₂R¹², SO₂R¹⁰, COR¹², lower alkyl and lower alkyl substituted by halogen, OR¹², oxo, CO₂R¹², C(O)NR⁵R⁶ or NR⁵R⁶,
heteroaryl,
heteroaryl substituted by the group halogen, CO₂R¹², SO₂R¹⁰, COR¹², lower alkyl and lower alkyl substituted by halogen, OR¹², oxo, CO₂R¹², C(O)NR⁵R⁶ or NR⁵R⁶,
NR⁵R⁶,
lower alkyl,
lower alkyl substituted by the group halogen, OR¹², oxo, CO₂R¹², C(O)NR⁵R⁶ or NR⁵R⁶, heterocycle, and
heterocycle substituted by the group $CO_2R^{12}$, $COR^{12}$, $SO_2R^{12}$, lower alkyl, $C(O)NR^5R^6$ or $NR^5R^6$;

X is selected from the group
S,
SO,
$SO_2$,
O; and n is 0, 1 or 2, or the pharmaceutically acceptable salts or esters thereof.

In another embodiment $R^1$ is a heterocycle that is substituted with H, lower alkyl, $S(O)_n R^{15}$, $CO_2R^7$, $COR^{12}$, $C(O)NR^{13}R^{14}$.

In another embodiment $R^1$ is a heterocycle that is substituted by lower alkyl that is substituted by aryl.

In another preferred embodiment, the invention relates to compounds of formula

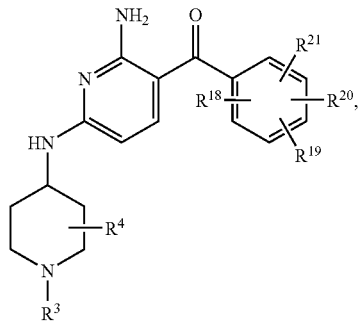

I(a)

wherein $R^3$ and $R^4$ are as defined above and $R^{18}$, $R^{19}$, $R^{20}$ and $R^{21}$ are each independently selected from lower alkyl, halogen and $OR^{12}$. The preferred halogens are F and Cl. Preferably, one of $R^{18}$-$R^{21}$ is $OR^{12}$, wherein $R^{12}$ is —$CH_3$, and most preferably the $OR^{12}$ substituent is on the number 2 carbon of the phenyl ring (see, e.g. the compounds of Examples 42 and 45).

Preferably, $R^3$ is selected from the group $CO_2R^7$, $COR^{12}$, $SO_2R^{15}$, $C(O)NR^5R^6$, lower alkyl and lower alkyl substituted by aryl, preferably phenyl. Most preferably, $R^3$ is $SO_2R^{15}$. Preferably, $R^{15}$ is lower alkyl or $NR^5R^6$.

Preferred $R^4$ groups include H, $OR^{11}$ and lower alkyl.

Preferred $R^5$ and $R^6$ groups are those wherein each is idependently selected from H and lower alkyl, or the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms and said ring atoms optionally being substituted by OH, oxo and $NH_2$, lower alkyl or lower alkyl substituted by The preferred $R^{12}$ is lower alkyl.

Examples of compounds of formula I(a) include:
[2-Amino-6-(1-methanesulfonyl-piperidin-4-ylamino)-pyridin-3-yl]-(2-methoxy-phenyl)-methanone (Example 6);
[2-Amino-6-(1-methanesulfonyl-piperidin-4-ylamino)-pyridin-3-yl]-(2-fluoro-phenyl)-methanone (Example 10);
4-[6-Amino-5-(2-fluoro-benzoyl)-pyridin-2-ylamino]-piperidine-1-carboxylic acid ethyl ester (Example 11);
[2-Amino-6-(1-ethanesulfonyl-piperidin-4-ylamino)-pyridin-3-yl]-(2-fluoro-phenyl)-methanone (Example 12);
1-{4-[6-Amino-5-(2-fluoro-benzoyl)-pyridin-2-ylamino]-piperidin-1-yl}-ethanone (Example 13);
1-{4-[6-Amino-5-(2-fluoro-benzoyl)-pyridin-2-ylamino]-piperidin-1-yl}-propan-1-one (Example 14);
4-[6-Amino-5-(2-fluoro-benzoyl)-pyridin-2-ylamino]-piperidine-1-carboxylic acid ethylamide (Example 15);
4-[6-Amino-5-(2-fluoro-benzoyl)-pyridin-2-ylamino]-piperidine-1-carboxylic acid methylamide (Example 16);
[2-Amino-6-(1-methanesulfonyl-piperidin-4-ylamino)-pyridin-3-yl]-(3-methoxy-phenyl)-methanone (Example 18);
4-[6-Amino-5-(5-fluoro-2-methoxy-benzoyl)-pyridin-2-ylamino]-piperidine-1-carboxylic acid ethyl ester (Example 20);
[2-Amino-6-(1-methanesulfonyl-piperidin-4-ylamino)-pyridin-3- yl]-(5-fluoro-2-methoxy-phenyl)-methanone (Example 23);
[2-Amino-6-(1-ethanesulfonyl-piperidin-4-ylamino)-pyridin-3-yl]-(5-fluoro-2-methoxy-phenyl)-methanone (Example 24);
{2-Amino-6-[1-(propane-1-sulfonyl)-piperidin-4-ylamino]-pyridin-3-yl}-(5-fluoro-2-methoxy-phenyl)-methanone (Example 25);
{2-Amino-6-[1-(propane-2-sulfonyl)-piperidin-4-ylamino]-pyridin-3-yl}-(5-fluoro-2-methoxy-phenyl)-methanone (Example 26);
4-[6-Amino-5-(5-fluoro-2-methoxy-benzoyl)-pyridin-2-ylamino]-piperidine-1-carboxylic acid methyl ester (Example 27);
4-[6-Amino-5-(5-fluoro-2-methoxy-benzoyl)-pyridin-2-ylamino]-piperidine-1-carboxylic acid propyl ester (Example 28);
[2-Amino-6-(1-benzyl-piperidin-4-ylamino)-pyridin-3-yl]-(5-fluoro-2-methoxy-phenyl)-methanone (Example 29);
1-{4-[6-Amino-5-(5-fluoro-2-methoxy-benzoyl)-pyridin-2-ylamino]-piperidin-1-yl}-ethanone (Example 30);
1-{4-[6-Amino-5-(5-fluoro-2-methoxy-benzoyl)-pyridin-2-ylamino]-piperidin-1-yl}-propan-1-one (Example 31);
4-[6-Amino-5-(5-fluoro-2-methoxy-benzoyl)-pyridin-2-ylamino]-piperidine-1-carboxylic acid methylamide (Example 32);
4-[6-Amino-5-(5-fluoro-2-methoxy-benzoyl)-pyridin-2-ylamino]-piperidine-1-carboxylic acid ethylamide (Example 33);
[2-Amino-6-(1-methyl-piperidin-4-ylamino)-pyridin-3-yl]-(5-fluoro-2-methoxy-phenyl)-methanone (Example 34);
[2-Amino-6-(1-methanesulfonyl-piperidin-4-ylamino)-pyridin-3-yl]-(4-methoxy-phenyl)-methanone (Example 36);
[2-Amino-6-(1-methanesulfonyl-piperidin-4-ylamino)-pyridin-3-yl]-(4-fluoro-phenyl)-methanone (Example 38); P [2-Amino-6-(1-methanesulfonyl-piperidin-4-ylamino)-pyridin-3-yl]-(2,3-difluoro-6-methoxy-phenyl)-methanone (Example 40);
4-[6-Amino-5-(2,3-difluoro-6-methoxy-benzoyl)-pyridin-2-ylamino]-piperidine-1-carboxylic acid ethyl ester (Example 41);
1-{4-[6-Amino-5-(2,3-difluoro-6-methoxy-benzoyl)-pyridin-2-ylamino]-piperidin-1-yl}-ethanone (Example 42);
1-{4-[6-Amino-5-(5-fluoro-2-methoxy-4-methyl-benzoyl)-pyridin-2-ylamino]-piperidin-1-yl}-ethanone (Example 44);
[2-Amino-6-(1-methanesulfonyl-piperidin-4-ylamino)-pyridin-3-yl]-(5-fluoro-2-methoxy-4-methyl-phenyl)-methanone (Example 45);

4-[6-Amino-5-(5-fluoro-2-methoxy-4-methyl-benzoyl)-pyridin-2-ylamino]-piperidine-1-carboxylic acid ethyl ester (Example 46);

1-{4-[6-Amino-5-(4-chloro-5-fluoro-2-methoxy-benzoyl)-pyridin-2-ylamino]-piperidin-1-yl}-ethanone (Example 48);

[2-Amino-6-(1-methanesulfonyl-piperidin-4-ylamino)-pyridin-3-yl]-(4-chloro-5-fluoro-2-methoxy-phenyl)-methanone (Example 49);

4-[6-Amino-5-(5-fluoro-2-methoxy-4-chloro-benzoyl)-pyridin-2-ylamino]-piperidine-1-carboxylic acid ethyl ester (Example 50); and

[2-Amino-6-(1-methanesulfonyl-piperidin-4-ylamino)-pyridin-3-yl]-(2,6-difluoro-phenyl)-methanone (Example 52).

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to the below described synthetic route (Scheme 1).

The commercially available starting material, 2,6-dichloronicotinic acid (from Aldrich. In Examples 1 and 2), can be regio-selectively converted to 2-amino-6-chloro-N-methoxy-N-methylnicotinamide (Example 3) via 2-amino-6-chloronicotinic acid or 2,6-dichloro-N-methoxy-N-methylnicotinamide as the intermediates (F. Mutterer and C. Weis, *Helvetica Chimica Acta*, 59, 1976, 222-229). The $R^2$ group is introduced by reaction with organolithium reagents that are either commercially available or, readily prepared from commercially available halides or substituted benzene. The final compounds of the invention are then obtained by displacement of the 6-chloro group with a variety of commercially available amines ($R^1NH_2$). When not commercially available, these reactants are prepared or cited in the individual examples.

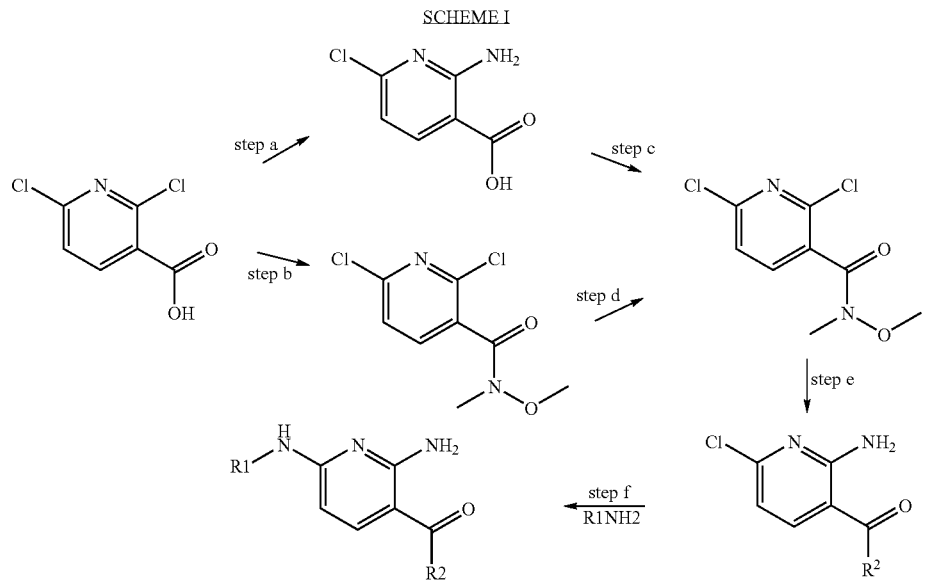

SCHEME I wherein $R^1$ and $R^2$ are as defined above.

Separating a Mixture of Stereoisomers Into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87-124).

Converting a Compound of Formula I that Bears a Basic Nitrogen Into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I that Bears a Carboxylic Acid Group Into a Pharmaceutically Acceptable Alkali Metal Salt The optional conversion of a compound of formula I that bears a carboxylic acid group into a pharmaceutically acceptable alkali metal salt can be effected by conventional means.

For example, the compound can be treated with an inorganic base such as lithium hydroxide, sodium hydroxide, potassium hydroxide, or the like.

Converting a Compound of Formula I that Bears a Carboxylic Acid Group Into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0-10 mole %) of N,N-dimethylaminopyridine, in an inert solvent such as a halogenated hydrocarbon (e.g., dichloromethane) at a temperature between about 0 degrees and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degrees.

Compositions/Formulations

In an alternative embodiment, the present invention includes pharmaceutical compositions comprising at least one compound of formula I, or a pharmaceutically acceptable salt or ester thereof and an a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase II inhibitors such as etoposide: topoisomerase I inhibitors such as CPT-11 or topotecan; tublin interacting agents, such as paclitaxel, docetaxel or epothilones; hormonal agents such as tamoxifen: thymidilaate synthaes inhibitors, such as 5-fluorouracil; and antimetabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early cdk1 inhibitor olomucine has been found to act synergistically with well known cytotoxic agents in inducing apoptosis. (*J. Cell Sci.,* 1995, 108, 2897-2904). Compounds of formula I may also be administered sequentially with known anticancer or cytotoxic agents when concommitant administration or a combination is inappropriate. This invention is not limited in the sequence of administration: compounds of formula I may be administered either prior to or after administration of the known anticancer or cytotoxic agent. For example, the cytotoxic activity of the cdk inhibitor flavopiridol is affected by the sequence of administration with anticancer agents. (*Cancer Research,* 1997, 57, 3375).

Starting Materials

In another embodiment, the present invention also relates to novel intermediates useful in the preparation of compounds of formula I. These novel intermediates include the following compounds:

2,6-Dichloro-N-methoxy-N-methyl-nicotinamide (Example 1);
2-Amino-6-chloro-nicotinic acid (Example 2);
2-Amino-6-chloro-N-methoxy-N-methyl-nicotinamide (Example 3);
(2,6-Dichloro-pyridin-3-yl)-(2-methoxy-phenyl)-methanone (Example 4);
(2-Amino-6-chloro-pyridin-3-yl)-(2-methoxy-phenyl)-methanone (Example 5);
(2-Amino-6-chloro-pyridin-3-yl)-(2-fluoro-phenyl)-methanone (Example 7);
4-[6-Amino-5-(2-fluoro-benzoyl)-pyridin-2-ylamino]-piperidine-1-carboxylic acid tert-butyl ester (Example 8);
[2-Amino-6-( piperidin-4-ylamino)-pyridin-3-yl]-(2-fluoro-phenyl)-methanone (Example 9);
(2-Amino-6-chloro-pyridin-3-yl)-(3-methoxy-phenyl)-methanone (Example 17);
(2-Amino-6-chloro-pyridin-3-yl)-(5-fluoro-2-methoxy-phenyl)-methanone (Example 19);
4-[6-Amino-5-(5-fluoro-2-methoxy-benzoyl)-pyridin-2-ylamino]-piperidine-1-carboxylic acid tert-butyl ester (Example 21);
[4-amino-2-(piperidin-4-ylamino)-pyrimidin-5-yl]-(5-fluoro-2-methoxy-phenyl)-methanone trifluoroacetic acid salt (Example 22);
(2-Amino-6-chloro-pyridin-3-yl)-(4-methoxy-phenyl)-methanone (Example 35);
(2-Amino-6-chloro-pyridin-3-yl)-(4-fluoro-phenyl)-methanone (Example 37);
(2-Amino-6-chloro-pyridin-3-yl)-(2,3-difluoro-6-methoxy-phenyl)-methanone (Example 39);
(2-Amino-6-chloro-pyridin-3-yl)-(5-fluoro-2-methoxy-4-methyl-phenyl)-methanone (Example 43);
(2-Amino-6-chloro-pyridin-3-yl)-(4-chloro-5-fluoro-2-methoxy-phenyl)-methanone (Example 47); and
(2-Amino-6-chloro-pyridin-3-yl)-(2,6-difluoro-phenyl)-methanone (Example 51).

EXAMPLES

The following examples illustrate preferred methods for synthesizing and using the compounds and formulations of the present invention. These examples and preparations are illustrative and are not intended to be limiting. It should be understood that there may be other embodiments which fall within the spirit and scope of the invention as defined by the claims appended hereto.

Example 1

2,6-Dichloro-N-methoxy-N-methyl-nicotinamide (RO4808591-000) (35031-8)

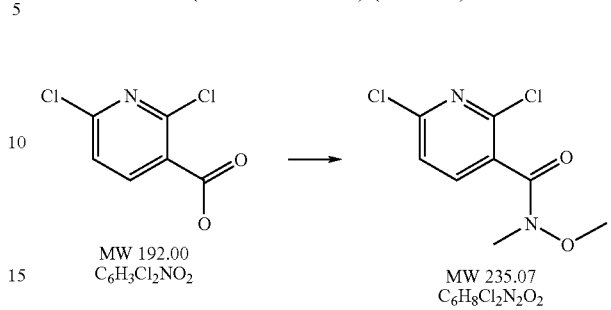

MW 192.00
$C_6H_3Cl_2NO_2$

MW 235.07
$C_6H_8Cl_2N_2O_2$

To a solution of 2,6-dichloronicotinic acid (500 mg, 2.63 mmol, Aldrich 90%) in anhydrous N,N-dimethylformamide (5 mL) were added O-benzotriazol-1-yl-N,N,N',N'-tetramethyluronium hexafluorophosphate (1.28 g, 3.37 mmol, Aldrich), 1-hydroxybenzotriazole hydrate (456 mg, 3.37 mmol, Aldrich) followed by N,N-diisopropylethylamine (1.3 g, 10.0 mmol) and N,O-dimethylhydroxylamine hydrochloride (306 mg, 3.15 mmol, Aldrich) at 0° C. The reaction was stirred for 1-2 hrs, treated with water and extracted with ethyl acetate. The combined organic extracts were washed with brine, dried and concentrated. The crude product was purified on silica gel with hexanes/ethyl acetate to give 2,6-Dichloro-N-methoxy-N-methyl-nicotinamide as a white solid (304.5 mg, 50% yield). HRMS, observed: 233.9968, Calcd for M+: 233.9963

Example 2

2-Amino-6-chloro-nicotinic acid

MW 192.00
$C_6H_3Cl_2NO_2$

MW 172.57
$C_6H_5ClN_2O_2$

A solution of 2,6-dichloronicotinic acid (10 g, 46.9 mmol, Aldrich 90%) was dissolved in concentrated ammonium hydroxide (100 mL, 29.4%, Fisher) and heated at 130-160° C. in a pressure bottle for 1-2 days before solvent was removed in vacuo. The residue was treated with water and the pH was lowered to ~8 with concentrated hydrochloric acid. The resulting mixture was extracted with ethyl acetate and the combined organic extracts were washed with brine, dried, concentrated and the crude product was recrystallized from ethyl acetate to give 2-Amino-6-chloro-nicotinic acid as white crystalline (2.74g, 34 % yield). HRMS, observed: 172.0042, Calcd for M+: 172.0040

Example 3

2-Amino-6-chloro-N-methoxy-N-methyl-nicotinamide

Method 1

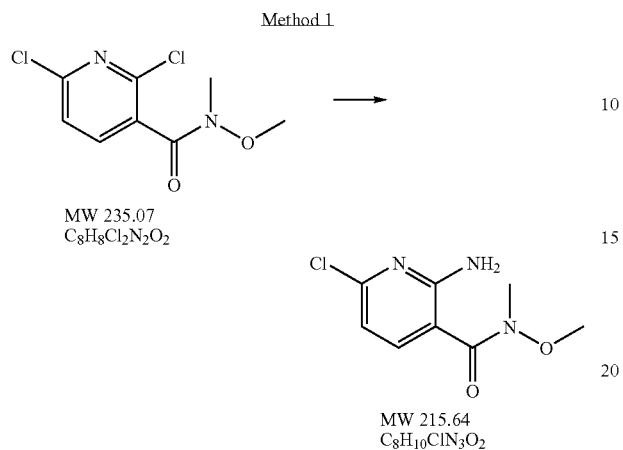

2,6-Dichloro-N-methoxy-N-methyl-nicotinamide (202.4 mg, 0.8610 mmol, Example 1) and concentrated ammonium hydroxide (1.8 mL, 29.4%, Fisher) in tetrahydrofuran (2.5 mL) were heated to 155° C. in the microwave for 2 hr. The reaction mixture was concentrated and the residue was purified on silica gel with hexanes/ethyl acetate to give 2-Amino-6-chloro-N-methoxy-N-methyl-nicotinamide (14.3 mg, 8% yield). HRMS, observed: 215.0463, Calcd for M$^+$: 215.0462.

Method 2:

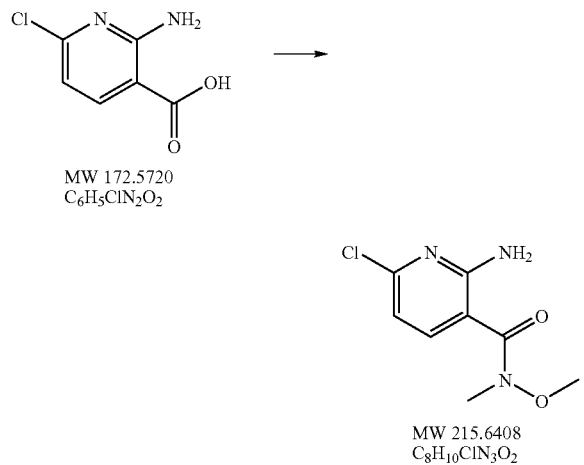

To a solution of 2-Amino-6-chloro-nicotinic acid (4.99g, 28.965 mmol, Example 2) in anhydrous N,N-dimethylformamide (50 mL) were added 1-hydroxybenzotriazole hydrate (6.21g, 40.57 mmol, Advanced ChemTech) and O-benzotriazol-1-yl-N,N,N',N'-tetramethyluroniumhexafluorophosphate (15.38 g, 40.5648 mmol, Aldrich) at 0° C. A solution of N,O-dimethylhydroxylamine hydrochloride (306 mg, 3.15 mmol, Aldrich) in anhydrous N,N-dimethylformamide (15 mL) was treated with N,N-diisopropylethylamine (8.28 g, 64.1 mmol) and immediately added to the reaction which was stirred at 0° C. for ~10 minutes then at room temperature for 4-5 hrs. The reaction was diluted with ethyl acetate (150 mL) and water (100 mL) and the aqueous layer was extracted with ethyl acetate (3×150 mL). The combined organic layers were washed with water (3×) and saturated sodium chloride, dried and concentrated. The crude product was purified on silica gel with 90/10→70/30 of hexanes/ethyl acetate to give 2-Amino-6-chloro-N-methoxy-N-methyl-nicotinamide (4.72 g, 21.92 mmol, 75.7 % yield). HRMS, observed: 215.0463, Calcd for M$^+$: 215.0462.

Example 4

(2,6-Dichloro-pyridin-3-yl)-(2-methoxy-phenyl)-methanone

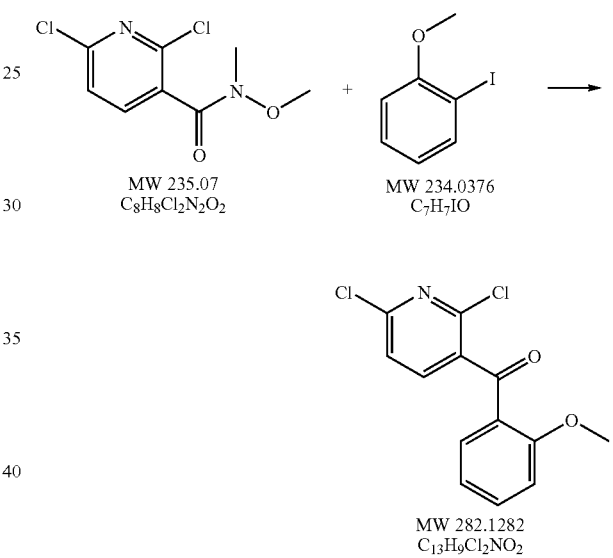

To a solution of 2-iodoanisole (4.97g, 21.24 mmol, Aldrich 98%) in anhydrous tetrahydrofuran (33 mL) at −78° C., was added a solution of n-butyllithium in hexane (2.5 M, 8.5 mL, 21.25 mmol, Aldrich). The reaction was stirred at −78 OC for 0.5-1 hr to give a solution of the 2-methoxyphenyl lithium for the following reaction.

To a solution of 2,6-Dichloro-N-methoxy-N-methyl-nicotinamide (503.3 mg, 2.141 mmol, Example 1) in anhydrous tetrahydrofuran (8 mL) was added a solution of freshly prepared 2-methoxyphenyl lithium (3-5 equiv, from above) and the reaction was stirred at −78° C. for 30-60 mins until the complete consumption of starting material. The resulting mixture was quenched with aqueous ammonium chloride solution, extracted with ethyl acetate, washed with saturated sodium chloride, dried over sodium sulfate and evaporated in vacuo. The residue was purified on silica gel with hexanes/ethyl acetate to give (2,6-Dichloro-pyridin-3-yl)-(2-methoxy-phenyl)-methanone as a light brown waxy solid (314.3 mg, 52% yield). HRMS, observed: 281.0023, Calcd for M$^+$: 281.0010.

Example 5

(2-Amino-6-chloro-pyridin-3-yl)-(2-methoxy-phenyl)-methanone

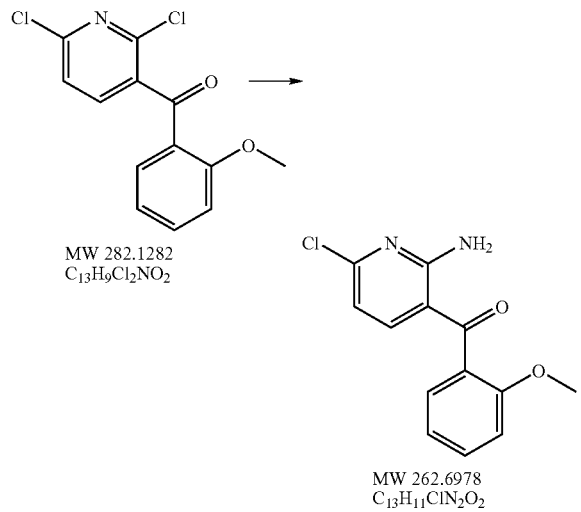

A solution of (2,6-Dichloro-pyridin-3-yl)-(2-methoxyphenyl)-methanone (50.3 mg, 0.178 mmol, Example 4) in 1,4-dioxane (2 mL) was treated with concentrated ammonium hydroxide (0.24 mL, 29.4%) and heated to 150° C. in the microwave for 3 hrs. The resulting mixture was treated with water and ethyl acetate, washed with saturated sodium chloride, dried over sodium sulfate and evaporated in vacuo. The residue was purified on silica gel with hexanes/ethyl acetate to give (2-Amino-6-chloro-pyridin-3-yl)-(2-methoxy-phenyl)-methanone as a off-white solid (23.7 mg, 50.7% yield). HRMS, observed: 262.0502, Calcd for M+: 262.0509.

Example 6

[2-Amino-6-(1-methanesulfonyl-piperidin-4-ylamino)-pyridin-3-yl]-(2-methoxy-phenyl)-methanone

A. Preparation of Methanesulfonyl-piperidin-4-ylamine with Trifluoro-acetic Acid

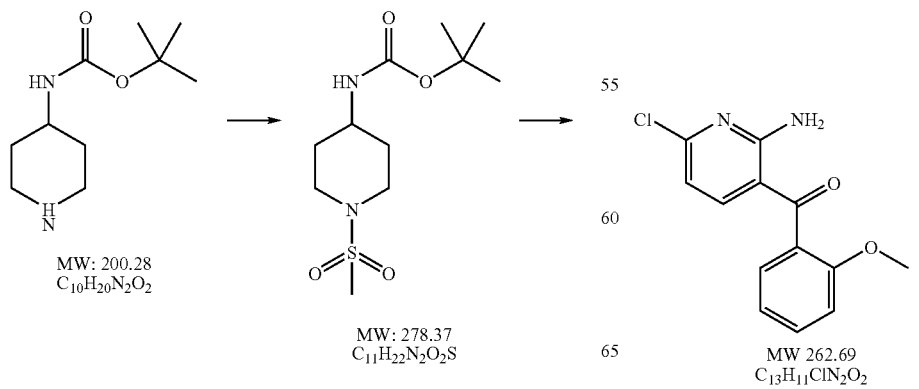

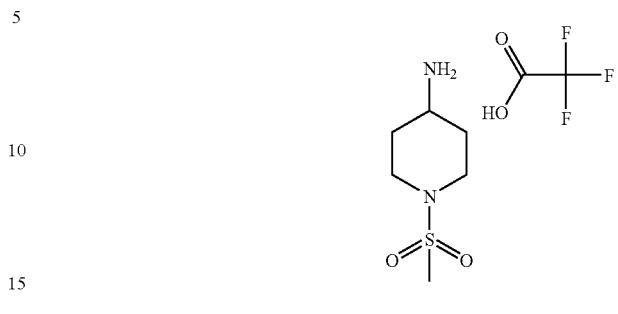

A solution of piperidin-4-yl-carbamic acid tert-butyl ester (1.0 g, 5.0 mmol, Astratech, Inc.) and diisopropylethylamine (4 mL) in tetrahydrofuran (40 mL) was stirred at +5° C. To this was added methanesulfonyl chloride (1.0 g, 8.8 mmol) in a bolus. The reaction was brought to room temperature for 1 hour, poured into water and extracted into methylene chloride (2×50 mL). The combined organic extracts were washed with 5% aqueous sodium bicarbonate. The organic solution was dried (Na$_2$SO$_4$) and solvent was removed under vacuum to give a crude solid. Purification was by trituration with ether/hexane to give (1-methanesulfonyl-piperidin4-yl)-carbamic acid tert-butyl ester as a white solid. Mass spectrum (ES) H+: 278

A suspension of (1-methanesulfonyl-piperidin-4-yl)-carbamic acid tert-butyl ester (1.14 g, 4.1 mmol, from above) in methylene chloride (15 mL) was treated at room temperature with trifluoroacetic acid (5.3 mL). After stirring for 2 hours, all solvent was removed and the residue was triturated with ether. This was filtered, washed with ether and dried in vacuum to give 1-methanesulfonyl-piperidin-4-ylamine; compound with trifluoro-acetic acid (1.20 g, 100% yield). HRMS, observed: 177.0692; Calcd for M+: 177.0698.

B). [2-Amino-6-(1-methanesulfonyl-piperidin-4-ylamino)-pyridin-3-yl]-(2-methoxy-phenyl)-methanone -continued

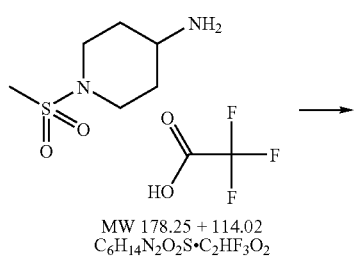

MW 178.25 + 114.02
C₆H₁₄N₂O₂S•C₂HF₃O₂

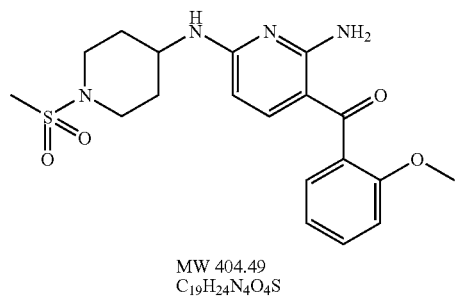

MW 404.49
C₁₉H₂₄N₄O₄S

A mixture of (2-Amino-6-chloro-pyridin-3-yl)-(2-methoxy-phenyl)-methanone (24.9 mg, 0.0948 mmol, Example 5), 1-methanesulfonyl-piperidin-4-ylamine (50.6 mg, 0.284 mmol, from Step A above), N,N-diisopropylethylamine (38mg, 0.294 mmol) and ethanol (2.7 mL) were heated at 160-180° C. in a sealed tube under microwave conditions for 0.5-4 hrs. The resulting reaction mixture was concentrated in vacuo and the residue was purified on silica gel with methylene chloride/methanol to give [2-Amino-6-(1-methanesulfonyl-piperidin4-ylamino)-pyridin-3-yl]-(2-methoxy-phenyl)-methanone as a white solid (22.5 mg, 58% yield). HRMS, observed: 405.1594, calcd for (M+H)⁺: 405.1591.

Example 7

(2-Amino-6-chloro-pyridin-3-yl)-(2-fluoro-phenyl)-methanone

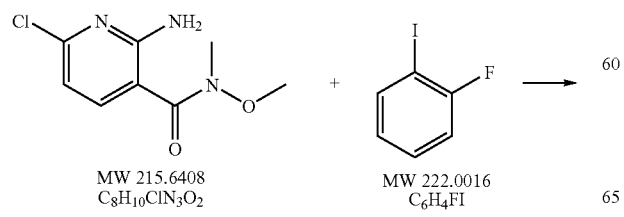

MW 215.6408
C₈H₁₀ClN₃O₂

MW 222.0016
C₆H₄FI

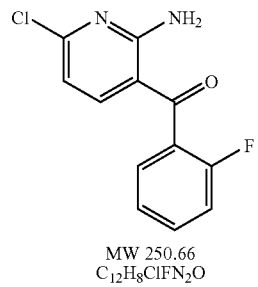

MW 250.66
C₁₂H₈ClFN₂O

2-Amino-6-chloro-N-methoxy-N-methyl-nicotinamide (500 mg, 2.32 mmol, Example 3) was dissolved in anhydrous tetrahydrofuran (14 mL) and cooled to −78° C. A solution of 2-fluorophenyl lithium (4-6 equiv, freshly prepared following the same procedure as in Example 4) was added. The reaction was stirred at −78° C. for 1-3 hrs and quenched with aqueous ammonium chloride solution. The resulting mixture was extracted with ethyl acetate, washed with saturated sodium chloride, dried over sodium sulfate and evaporated in vacuo. The product was then purified on silica gel to give (2-Amino-6-chloro-pyridin-3-yl)-(2-fluoro-phenyl)-methanone as a white solid (445.5 mg, 77% yield). HRMS, observed: 250.0306, Calcd for M⁺: 250.0309.

Example 8

4-[6-Amino-5-(2-fluoro-benzoyl)-pyridin-2-ylamino]-piperidine-1-carboxylic acid tert-butyl ester

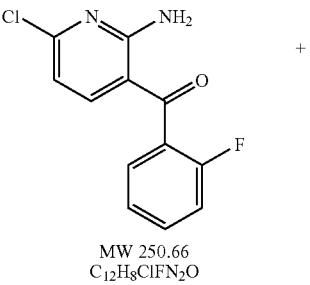

MW 250.66
C₁₂H₈ClFN₂O

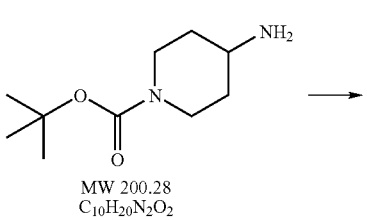

MW 200.28
C₁₀H₂₀N₂O₂

-continued

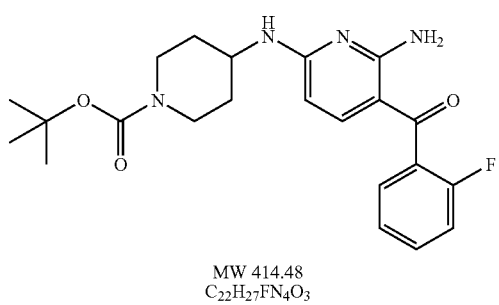

MW 414.48
$C_{22}H_{27}FN_4O_3$

The title compound was prepared from (2-Amino-6-chloro-pyridin-3-yl)-(2-fluoro-phenyl)-methanone (Example 7) and 4-amino-1-N-Boc-piperidine (Astatech, >96%) using the procedure described in Step B, Example 6. HRMS, observed: 415.2143, Calcd for (M+H)$^+$: 415.2140.

Example 9

[2-Amino-6-(piperidin-4-ylamino)-pyridin-3-yl]-(2-fluoro-phenyl)-methanone

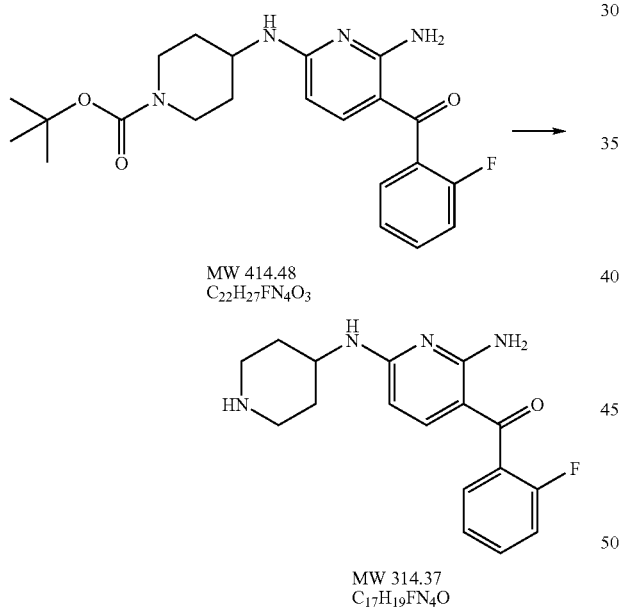

MW 414.48
$C_{22}H_{27}FN_4O_3$

MW 314.37
$C_{17}H_{19}FN_4O$

4-[6-Amino-5-(2-fluoro-benzoyl)-pyridin-2-ylamino]-piperidine-1-carboxylic acid tert-butyl ester (269.6 mg, 0.6504 mmol, Example 8) was dissolved in dichloromethane (5 mL), cooled to 0° C. and treated with trifluoroacetic acid (2.5 mL). After stirring ~30 minutes, the reaction mixture was concentrated in vacuo. The salt was then neutralized with saturated sodium carbonate (~3 mL), extracted with ethyl acetate/methylene chloride (~50 mL), washed with saturated sodium chloride (~3 mL), dried over sodium sulfate and evaporated in vacuo to give [2-Amino-6-(piperidin-4-ylamino)-pyridin-3-yl]-(2-fluoro-phenyl)-methanone as an off-white solid (200 mg, 0.636 mmol, 98 % yield).

Example 10

[2-Amino-6-(1-methanesulfonyl-piperidin4-ylamino)-pyridin-3-yl]-(2-fluoro-phenyl)-methanone

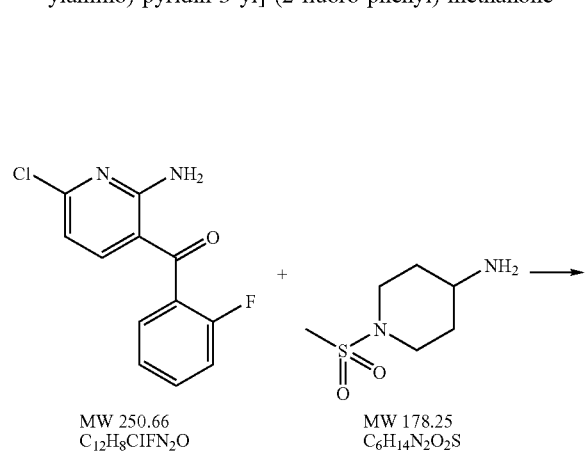

MW 250.66
$C_{12}H_8ClFN_2O$

MW 178.25
$C_6H_{14}N_2O_2S$

MW 392.46
$C_{18}H_{21}FN_4O_3S$

The title compound was prepared from (2-Amino-6-chloro-pyridin-3-yl)-(2-fluoro-phenyl)-methanone (Example 7) and 1-methanesulfonyl-piperidin-4-ylamine (Step A, Example 6) using the procedure described in Step B. Example 6. HRMS, observed: 392.1329, calcd for M$^+$: 392.1318.

Example 11

4-[6-Amino-5-(2-fluoro-benzoyl)-pyridin-2-ylamino]-piperidine-1-carboxylic acid ethyl ester

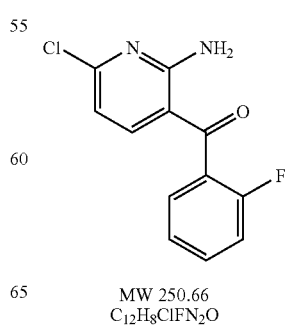

MW 250.66
$C_{12}H_8ClFN_2O$

-continued

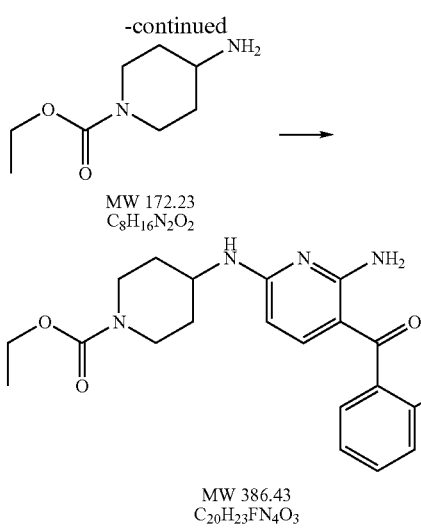

The title compound was prepared from (2-Amino-6-chloro-pyridin-3-yl)-(2-fluoro-phenyl)-methanone (Example 7) and ethyl-4-amino-1-piperidine carboxylate (Aldrich) using the procedure described in Step B, Example 6. HRMS, observed: 386.1762, calcd for M+: 386.1754.

Example 12

[2-Amino-6-(1-ethanesulfonyl-piperidin-4-ylamino)-pyridin-3-yl]-(2-fluoro-phenyl)-methanone

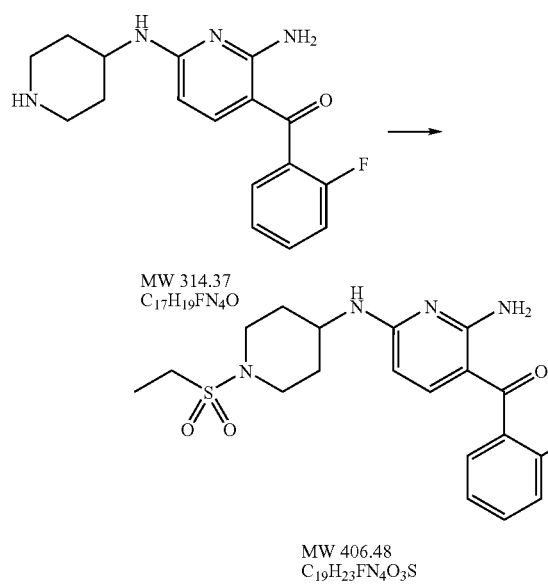

To a solution of [2-Amino-6-(piperidin-4-ylamino)-pyridin-3-yl]-(2-fluoro-phenyl)-methanone (19.2 mg, 0.0611 mmol, Example 9) in methylene chloride (1.5 mL) were added triethylamine (12.6 mg, 0.124 mmol, Aldrich) in methylene chloride (0.2 mL) and a solution of ethanesulfonyl chloride (8.66 mg, 0.066 mmol, Aldrich 99+%) in methylene chloride (0.2 mL) at room temperature. After ~30 mins the reaction mixture was concentrated and purified by reversed phase HPLC as described in Example 11 to give [2-Amino-6-(1-ethanesulfonyl-piperidin-4-ylamino)-pyridin-3-yl]-(2-fluoro-phenyl)-methanone as a white solid (15.1 mg, 60 % yield). HRMS, observed: 407.1533, calcd for (M+H)+: 407.1548.

Example 13

1-{4-[6-Amino-5-(2-fluoro-benzoyl)-pyridin-2-ylamino]-piperidin-1-yl}-ethanone

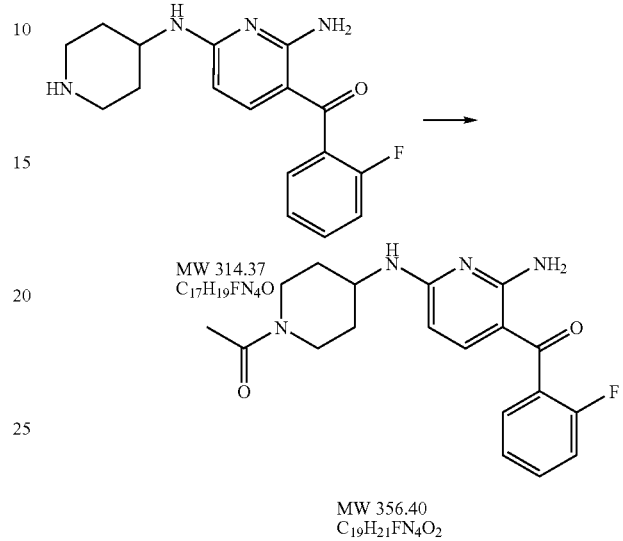

The title compound was prepared from [2-Amino-6-(piperidin-4-ylamino)-pyridin-3-yl]-(2-fluoro-phenyl)-methanone (Example 9) and acetyl chloride (Aldrich 98.5%) using the procedure described in Example 12. HRMS, observed: 356.1655, Calcd for M+: 356.1649.

Example 14

1-{4-[6-Amino-5-(2-fluoro-benzoyl)-pyridin-2-ylamino]-piperidin-1-yl}-propan-1-one

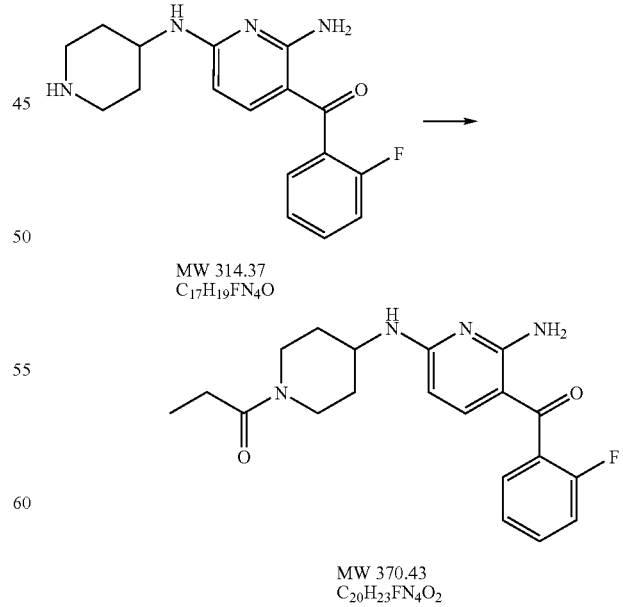

The title compound was prepared from [2-Amino-6-(piperidin-4-ylamino)-pyridin-3-yl]-(2-fluoro-phenyl)-methanone (Example 9) and propionyl chloride (Aldrich 98%) using the procedure described in Example 12. HRMS, observed: 370.1807, Calcd for M+: 370.1805.

Example 15

4-[6-Amino-5-(2-fluoro-benzoyl)-pyridin-2-ylamino]-piperidine-1-carboxylic acid ethylamide

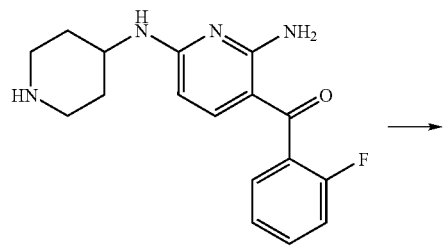

MW 314.37
C$_{17}$H$_{19}$FN$_4$O

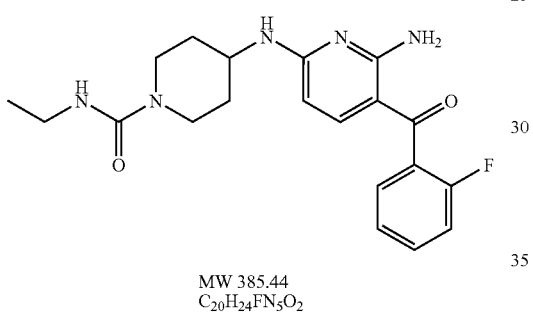

MW 385.44
C$_{20}$H$_{24}$FN$_5$O$_2$

The title compound was prepared from [2-Amino-6-(piperidin-4-ylamino)-pyridin-3-yl]-(2-fluoro-phenyl)-methanone (Example 9) and ethyl isocyanate (Aldrich 98%) using the procedure described in Example 12. HRMS, observed: 385.1917, calcd for M+: 385.1914.

Example 16

4-[6-Amino-5-(2-fluoro-benzoyl)-pyridin-2-ylamino]-piperidine-1-carboxylic acid methylamide

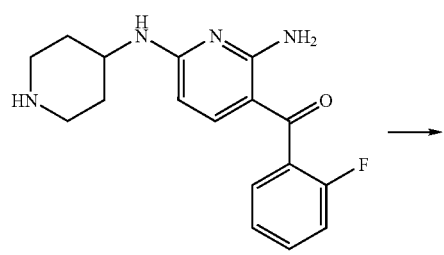

MW 314.37
C$_{17}$H$_{19}$FN$_4$O

-continued

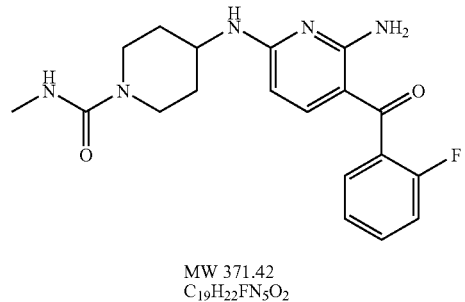

MW 371.42
C$_{19}$H$_{22}$FN$_5$O$_2$

The title compound was prepared from [2-Amino-6-(piperidin-4-ylamino)-pyridin-3-yl]-(2-fluoro-phenyl)-methanone (Example 9) and methyl isocyanate (Aldrich 98%) using the procedure described in Example 12. HRMS, observed: 371.1756, calcd for M+: 371.1758.

Example 17

(2-Amino-6-chloro-pyridin-3-yl)-(3-methoxy-phenyl)-methanone

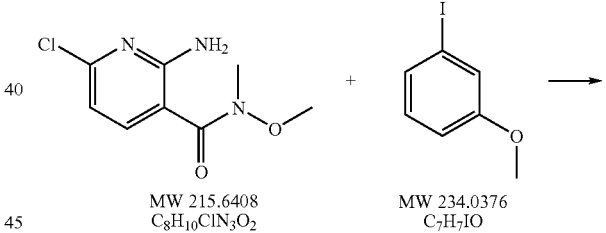

MW 215.6408
C$_8$H$_{10}$ClN$_3$O$_2$

MW 234.0376
C$_7$H$_7$IO

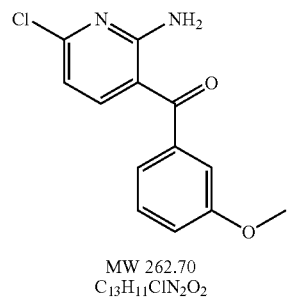

MW 262.70
C$_{13}$H$_{11}$ClN$_2$O$_2$

The title compound was prepared from 2-Amino-6-chloro-N-methoxy-N-methyl-nicotinamide (Example 3) and 3-iodoanisole (Aldrich) using the procedure described in Example 7. HRMS, observed: 262.0514, Calcd for M+: 262.0509.

Example 18

[2-Amino-6-(1-methanesulfonyl-piperidin-4-ylamino)-pyridin-3-yl]-(3-methoxy-phenyl)-methanone

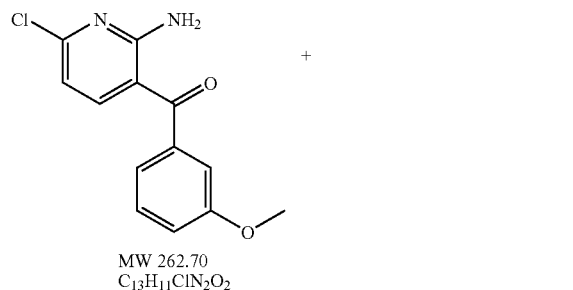

The title compound was prepared from (2-Amino-6-chloro-pyridin-3-yl)-(3-methoxy-phenyl)-methanone (Example 17) and 1-methanesulfonyl-piperidin-4-ylamine (Step A, Example 6) using the procedure described in Step B. Example 6. HRMS, 405.1595 observed:, Calcd for (M+H)⁺: 405.1591.

Example 19

(2-Amino-6-chloro-pyridin-3-yl)-(5-fluoro-2-methoxy-phenyl)-methanone

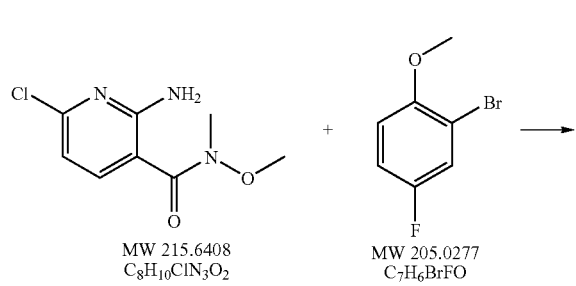

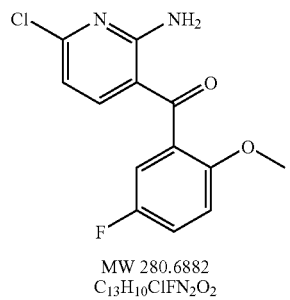

The title compound was prepared from 2-Amino-6-chloro-N-methoxy-N-methyl-nicotinamide (Example 3) and 2-bromo-4-fluoroanisole (Aldrich) using the procedure described in Example 7. HRMS, observed: 280.0417, Calcd for M⁺: 280.0415.

Example 20

4-[6-Amino-5-(5-fluoro-2-methoxy-benzoyl)-pyridin-2-ylamino]-piperidine-1-carboxylic acid ethyl ester

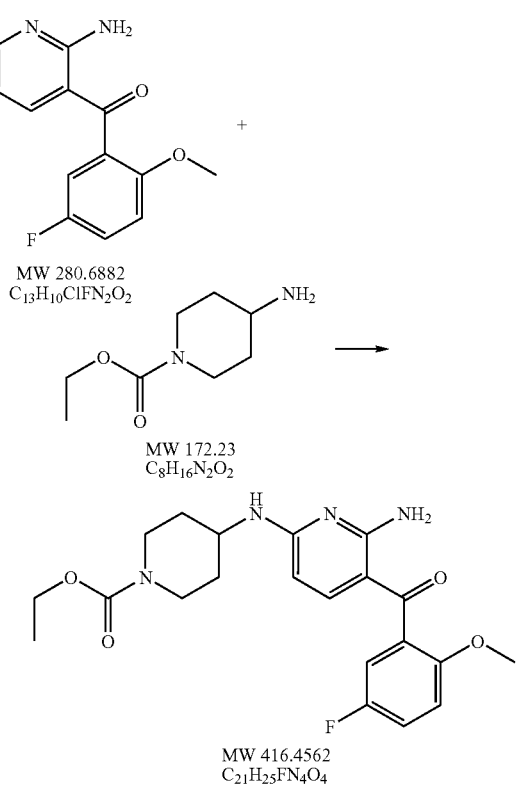

The title compound was prepared from (2-Amino-6-chloro-pyridin-3-yl)-(5-fluoro-2-methoxy-phenyl)-methanone (Example 19) and ethyl-4-amino-1-piperidine carboxylate (Aldrich 96) using the procedure described in Step B. Example 6. HRMS, observed: 417.1938, Calcd for (M+H)⁺: 417.1933.

Example 21

4-[6-Amino-5-(5-fluoro-2-methoxy-benzoyl)-pyridin-2-ylamino]-piperidine-1-carboxylic acid tert-butyl ester

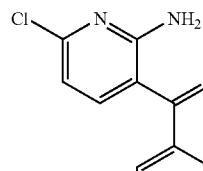

MW 280.6882
$C_{13}H_{10}ClFN_2O_2$

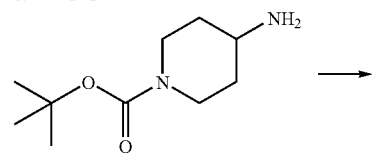

MW 200.2831
$C_{10}H_{20}N_2O_2$

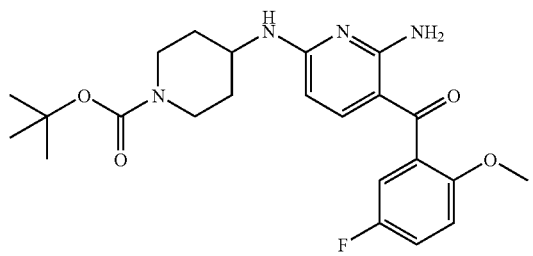

MW 444.5104
$C_{23}H_{29}FN_4O_4$

The title compound was prepared from (2-amino-6-chloropyridin-3-yl)-(5-fluoro-2-methoxyphenyl)methanone (Example 19) and 4-amino-1-N-Bocpiperidine (Astatech, >96%) using the procedure described in Step B. Example 6. HRMS, observed: 445.2252, Calcd for (M+H)⁺: 445.2246.

Example 22

[4-amino-2-(piperidin-4-ylamino)-pyrimidin-5-yl]-(5-fluoro-2-methoxy-phenyl)-methanone trifluoroacetic acid salt

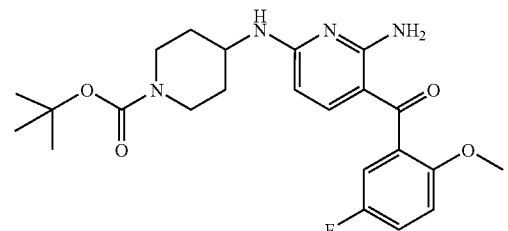

MW 444.5104
$C_{23}H_{29}FN_4O_4$

-continued

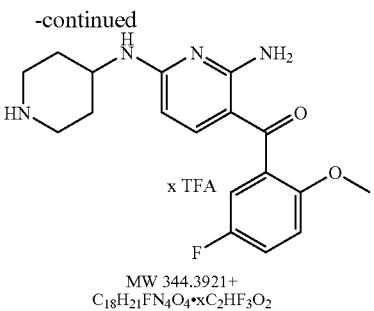

MW 344.3921+
$C_{18}H_{21}FN_4O_4 \cdot xC_2HF_3O_2$

A solution of 4-[6-amino-5-(5-fluoro-2-methoxy-benzoyl)-pyridin-2-ylamino]-piperidine-1-carboxylic acid tert-butyl ester (256.1 mg, 0.5761 mmol, Example 21) in dichloromethane (5 mL) was cooled to 0° C. and treated with trifluoroacetic acid (2.5 mL). After stirring 30 mins, the reaction mixture was concentrated in vacuo to give [4-amino-2-(piperidin-4-ylamino)-pyrimidin-5-yl]-(5-fluoro-2-methoxy-phenyl)-methanone as the trifluoroacetic acid salt (519.8 mg). MS (M+H)⁺: 345.

Example 23

[2-Amino-6-(1-methanesulfonyl-piperidin-4-ylamino)-pyridin-3-yl]-(5-fluoro-2-methoxy-phenyl)-methanone

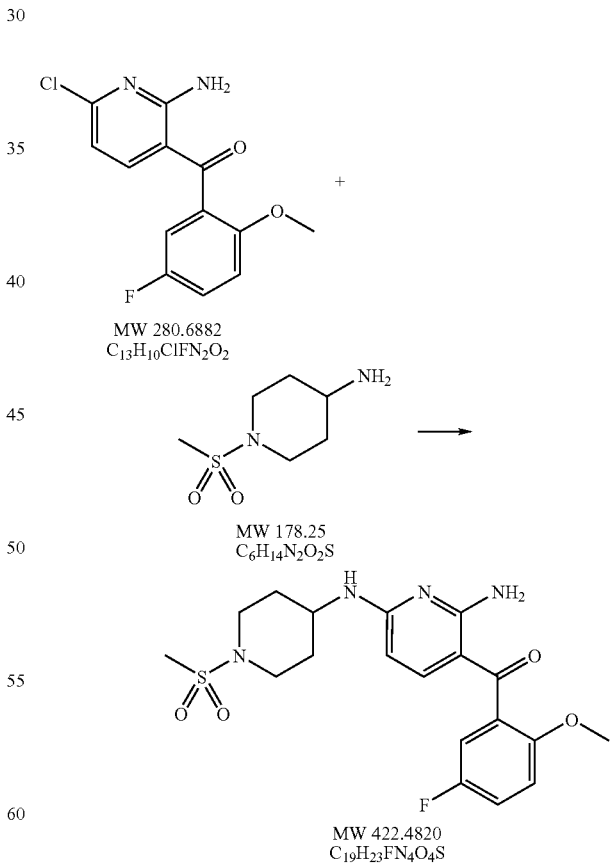

MW 280.6882
$C_{13}H_{10}ClFN_2O_2$

MW 178.25
$C_6H_{14}N_2O_2S$

MW 422.4820
$C_{19}H_{23}FN_4O_4S$

The title compound was prepared from (2-amino-6-chloropyridin-3-yl)-(5-fluoro-2-methoxyphenyl)methanone (Example 19) and 1-methanesulfonylpiperidin-4-ylamine (Step A. Example 6) using the procedure described in Step B.

Example 6. HRMS, observed: 423.1502, Calcd for (M+H)+: 423.1497. $K_i$ for cdk4=0.040 μM, cdk2=0.098 μM, and IC$_{50}$ for HCT116 cell line=9 μM.

Example 24

[2-Amino-6-(1-ethanesulfonyl-piperidin-4-ylamino)-pyridin-3-yl]-(5-fluoro-2-methoxy-phenyl)-methanone

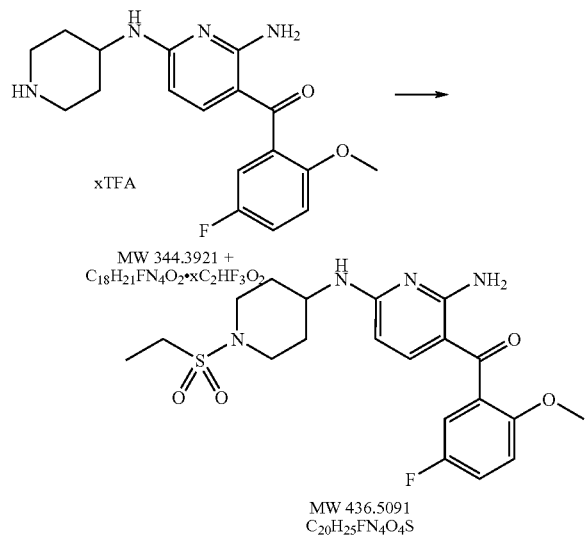

To a solution of [4-amino-2-(piperidin-4-ylamino)-pyrimidin-5-yl]-(5-fluoro-2-methoxy-phenyl)-methanone trifluoroacetic acid salt (0.0589 mmol, Example 22) in methylene chloride (1.25 mL) were added triethylamine (0.065 mL, 0.466 mmol, Aldrich) and a solution of ethanesulfonyl chloride (8.1 mg, 0.062 mmol, Aldrich 99+%) in methylene chloride (0.33 mL) at 0° C. After 5 minutes the reaction mixture was allowed to stir at room temperature for 1 hr before it was concentrated in vacuo. The residue was absorbed on silica gel and purified with 99.5/0.5495/5 of methylene chloride/methanol to give [2-amino-6-(1-ethanesulfonyl-piperidin-4-ylamino)-pyridin-3-yl]-(5-fluoro-2-methoxy-phenyl)-methanone as a white solid (16.0 mg, 63% yield). HRMS, observed: 437.1660, Calcd for (M+H)+: 437.1654.

Example 25

{2-Amino-6-[1-(propane-1-sulfonyl)-piperidin-4-ylamino]-pyridin-3-yl}-(5-fluoro-2-methoxy-phenyl)-methanone

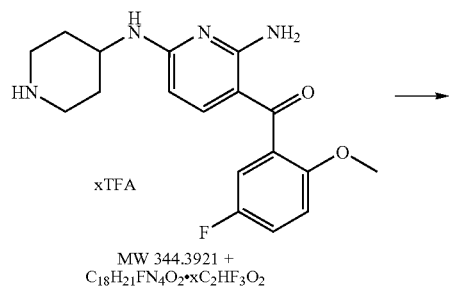

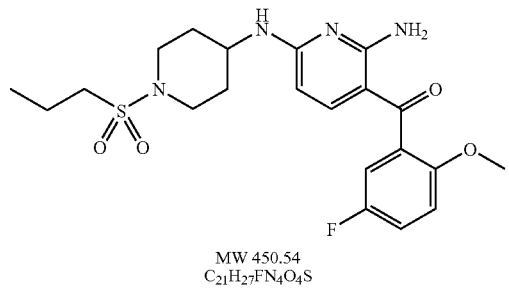

The title compound was prepared from [4-amino-2-(piperidin-4-ylamino)-pyrimidin-5-yl]-(5-fluoro-2-methoxy-phenyl)-methanone trifluoroacetic acid salt (Example 22) and 1-propanesulfonyl chloride (Aldrich 97%) using the procedure described in Example 24. HRMS, observed 451.1817, Calcd for (M+H)+: 451.1810.

Example 26

{2-Amino-6-[1-(propane-2-sulfonyl)-piperidin-4-ylamino]-pyridin-3-yl}-(5-fluoro-2-methoxy-phenyl)-methanone

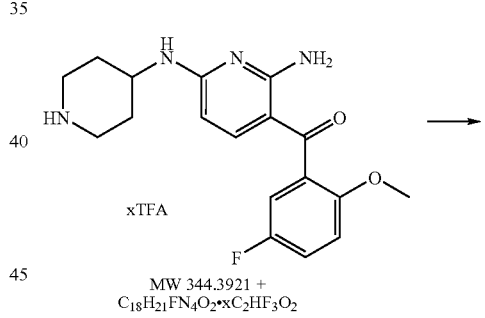

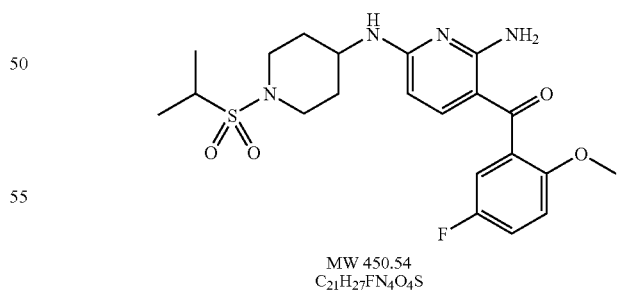

The title compound was prepared from [4-amino-2-(piperidin-4-ylamino)-pyrimidin-5-yl]-(5-fluoro-2-methoxy-phenyl)-methanone trifluoroacetic acid salt (Example 22) and isopropyl sulfonyl chloride (Aldrich 97%) using the procedure described in Example 24. HRMS, observed: 451.1814, Calcd for (M+H)+: 451.1810.

Example 27

4-[6-Amino-5-(5-fluoro-2-methoxy-benzoyl)-pyridin-2-ylamino]-piperidine-1-carboxylic acid methyl ester

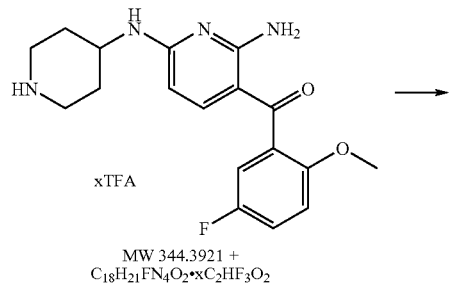

xTFA

MW 344.3921 +
$C_{18}H_{21}FN_4O_2 \cdot xC_2HF_3O_2$

→

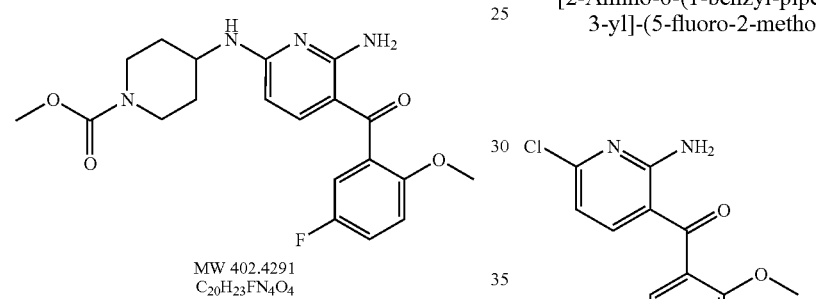

MW 402.4291
$C_{20}H_{23}FN_4O_4$

The title compound was prepared from [4-amino-2-(piperidin-4-ylamino)-pyrimidin-5-yl]-(5-fluoro-2-methoxy-phenyl)-methanone trifluoroacetic acid salt (Example 22) and methylchloroformate (Aldrich 99%) using the procedure described in Example 24. HRMS, observed: 403.1781, Calcd for (M+H)+: 403.1776.

Example 28

4-[6-Amino-5-(5-fluoro-2-methoxy-benzoyl)-pyridin-2-ylamino]-piperidine-1-carboxylic acid propyl ester

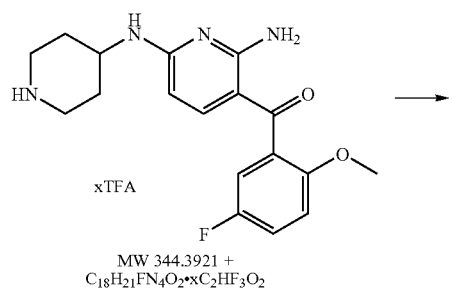

xTFA

MW 344.3921 +
$C_{18}H_{21}FN_4O_2 \cdot xC_2HF_3O_2$

→

-continued

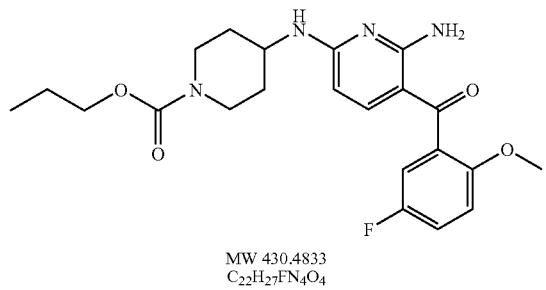

MW 430.4833
$C_{22}H_{27}FN_4O_4$

The title compound was prepared from [4-amino-2-(piperidin4-ylamino)-pyrimidin-5-yl]-(5-fluoro-2-methoxy-phenyl)-methanone trifluoroacetic acid salt (Example 22) and 1-propyl chloroformate (Aldrich 98%) using the procedure described in Example 24. HRMS, observed: 431.2095, Calcd for (M+H)+: 431.2089.

Example 29

[2-Amino-6-(1-benzyl-piperidin-4-ylamino)-pyridin-3-yl]-(5-fluoro-2-methoxy-phenyl)-methanone

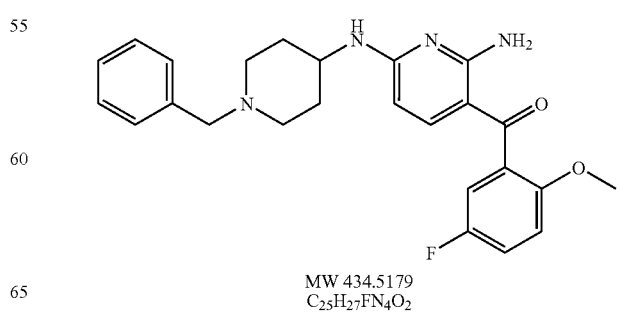

MW 280.6882
$C_{13}H_{10}ClFN_2O_2$

+

MW 190.2907
$C_{12}H_{18}N_2$

→

MW 434.5179
$C_{25}H_{27}FN_4O_2$

The title compound was prepared from (2-amino-6-chloropyridin-3-yl)-(5-fluoro-2-methoxyphenyl)methanone (Example 19) and 4-amino-1-benzylpiperidine (Ardrich) using the procedure described in Step B. Example 6. HRMS, observed: 435.2196, Calcd for (M+H)+: 435.2191.

Example 30

1-{4-[6-Amino-5-(5-fluoro-2-methoxy-benzoyl)-pyridin-2-ylamino]-piperidin-1-yl}-ethanone

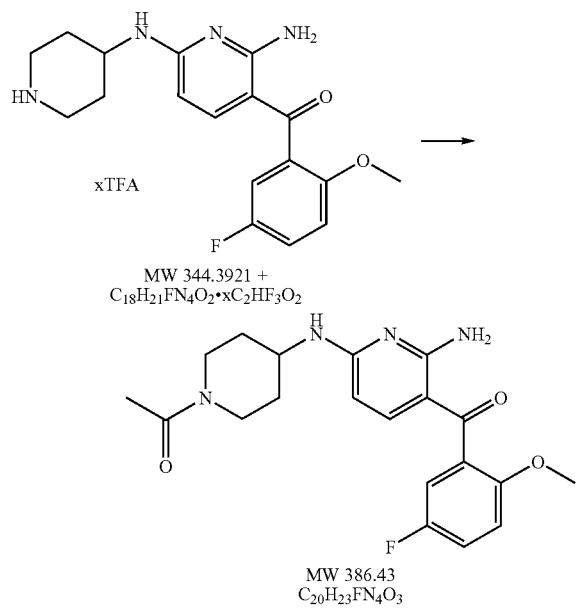

The title compound was prepared from [4-amino-2-(piperidin-4-ylamino)-pyrimidin-5-yl]-(5-fluoro-2-methoxyphenyl)-methanone trifluoroacetic acid salt (Example 22) and acetyl chloride (Aldrich 98.5%) using the procedure described in Example 24. HRMS, observed: 387.1833, Calcd for (M+H)+: 387.1827.

Example 31

1-{4-[6-Amino-5-(5-fluoro-2-methoxy-benzoyl)-pyridin-2-ylamino]-piperidin-1-yl}-propan-1-one

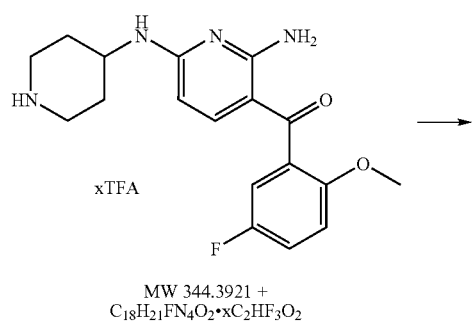

-continued

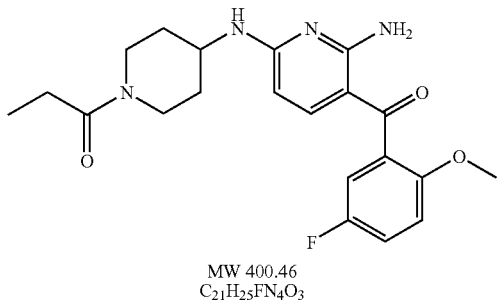

The title compound was prepared from [4-amino-2-(piperidin-4-ylamino)-pyrimidin-5-yl]-(5-fluoro-2-methoxyphenyl)-methanone trifluoroacetic acid salt (Example 22) and propionyl chloride (Aldrich 98%) using the procedure described in Example 24. HRMS, observed: 401.1988, Calcd for (M+H)+: 401.1984.

Example 32

4-[6-Amino-5-(5-fluoro-2-methoxy-benzoyl)-pyridin-2-ylamino]-piperidine-1-carboxylic acid methylamide

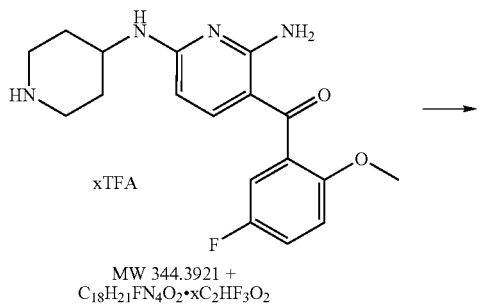

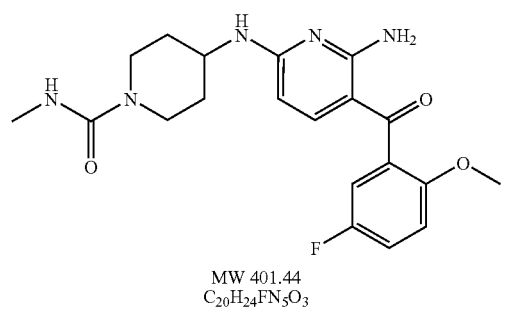

The title compound was prepared from [4-amino-2-(piperidin-4-ylamino)-pyrimidin-5-yl]-(5-fluoro-2-methoxyphenyl)-methanone trifluoroacetic acid salt (Example 22) and methyl isocyanate (Aldrich, 98%) using the procedure described in Example 24. HRMS, observed: 402.1940, Calcd for (M+H)+: 402.1936.

Example 33

4-[6-Amino-5-(5-fluoro-2-methoxy-benzoyl)-pyridin-2-ylamino]-piperidine-1-carboxylic acid ethylamide

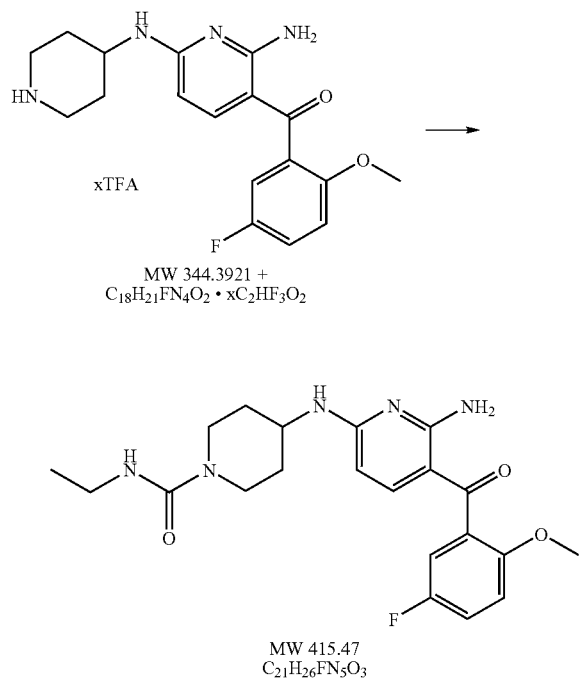

The title compound was prepared from [4-amino-2-(piperidin4-ylamino)-pyrimidin-5-yl]-(5-fluoro-2-methoxy-phenyl)-methanone trifluoroacetic acid salt (Example 22) and ethyl isocyanate (Aldrich 98%) using the procedure described in Example 24. HRMS, observed: 416.2097, Calcd for (M+H)$^+$: 416.2093.

Example 34

[2-Amino-6-(1-methyl-piperidin-4-ylamino)-pyridin-3-yl]-(5-fluoro-2-methoxy-phenyl)-methanone

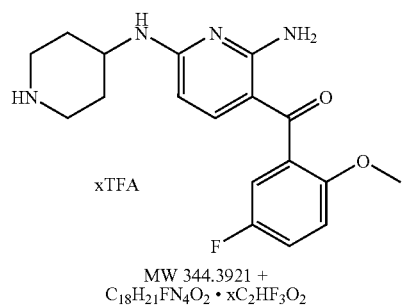

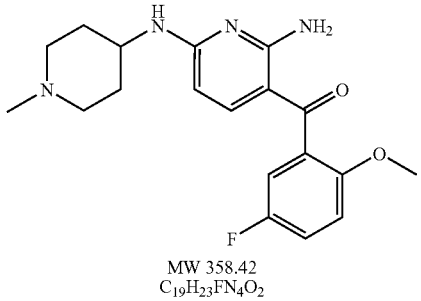

To a solution of [4-amino-2-(piperidin-4-ylamino)-pyrimidin-5-yl]-(5-fluoro-2-methoxy-phenyl)-methanone trifluoroacetic acid salt (0.0575 mmol, Example 22) in N,N-dimethylformamide (1.5 mL) were added potassium carbonate (55.6 mg, 0.4024 mmol, Aldrich) and iodomethane (14.8 mg, 0.104 mmol, Aldrich 99.5%) in N,N-dimethylformamide (0.35 mL). The reaction was stirred at 0° C. for 4 hrs. The resulting mixture was diluted with ethyl acetate (30 mL), washed with water, brine, dried over sodium sulfate and evaporated in vacuo. The residue was purified on reversed phase HPLC to give [2-Amino-6-(1-methyl-piperidin-4-ylamino)-pyridin-3-yl]-(5-fluoro-2-methoxy-phenyl)-methanone as a white solid (4.8 mg, 24% yield). HRMS, observed: 358.1810, Calcd for M$^+$: 358.1805.

Example 35

(2-Amino-6-chloro-pyridin-3-yl)-(4-methoxy-phenyl)-methanone

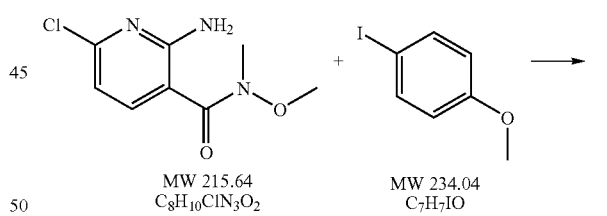

The title compound was prepared from 2-Amino-6-chloro-N-methoxy-N-methyl-nicotinamide (Example 3) and 4-methoxyphenyllithium freshly prepared from 4-iodoanisole (Aldrich) using the procedure described in Example 7. HRMS, observed: 262.0512, Calcd for M+: 262.0509.

Example 36

[2-Amino-6-(1-methanesulfonyl-piperidin-4-ylamino)-pyridin-3-yl]-(4-methoxy-phenyl)-methanone

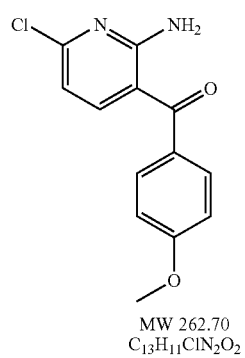

MW 262.70
$C_{13}H_{11}ClN_2O_2$

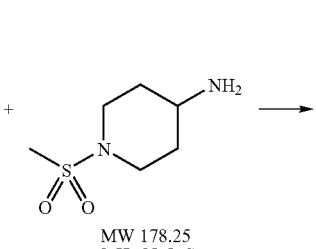

MW 178.25
$C_6H_{14}N_2O_2S$

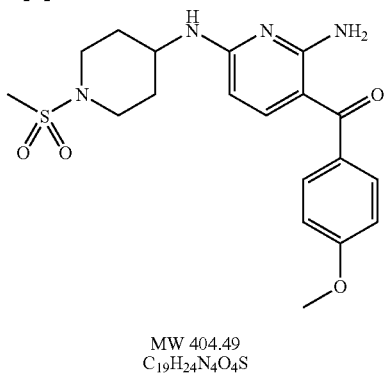

MW 404.49
$C_{19}H_{24}N_4O_4S$

The title compound was prepared from (2-Amino-6-chloro-pyridin-3-yl)-(4-methoxy-phenyl)-methanone (Example 35) and 1-methanesulfonyl-piperidin-4-ylamine (Step A, Example 6) using the procedure described in Step B. Example 6. HRMS, observed: 405.1595, calcd for (M+H)+: 405.1591.

Example 37

(2-Amino-6-chloro-pyridin-3-yl)-(4-fluoro-phenyl)-methanone

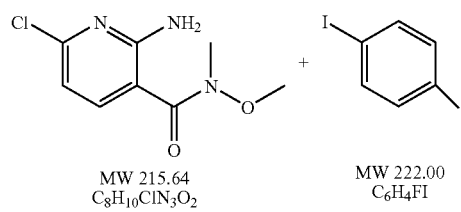

MW 215.64
$C_8H_{10}ClN_3O_2$

MW 222.00
$C_6H_4FI$

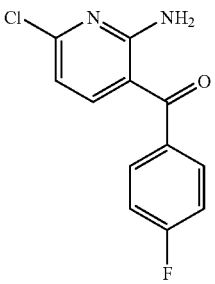

MW 250.66
$C_{12}H_8ClFN_2O$

The title compound was prepared from 2-Amino-6-chloro-N-methoxy-N-methyl-nicotinamide (Example 3) and 1-fluoro-4-iodobenzene (Aldrich 99%) using the procedure described in Example 7. HRMS, observed: 250.0314, Calcd for M+: 250.0309.

Example 38

[2-Amino-6-(1-methanesulfonyl-piperidin-4-ylamino)-pyridin-3-yl]-(4-fluoro-phenyl)-methanone

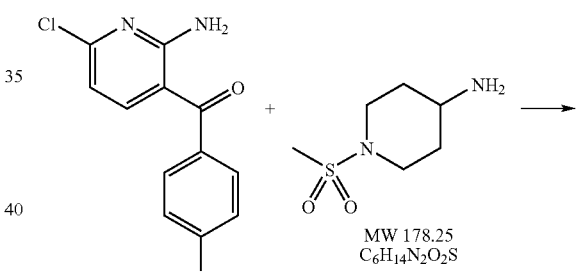

MW 250.66
$C_{12}H_8ClFN_2O$

MW 178.25
$C_6H_{14}N_2O_2S$

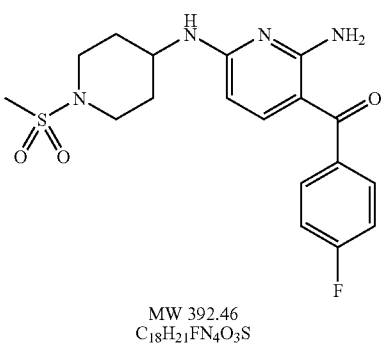

MW 392.46
$C_{18}H_{21}FN_4O_3S$

The title compound was prepared from (2-amino-6-chloro-pyridin-3-yl)-(4-fluorophenyl)methanone (Example 37) and 1-methanesulfonyl-piperidin-4-ylamine (Step A, Example 6) using the procedure described in Step B. Example 6. HRMS, observed: 393.1391, Calcd for (M+H)+: 393.1391.

Example 39

(2-Amino-6-chloro-pyridin-3-yl)-(2,3-difluoro-6-methoxy-phenyl)-methanone

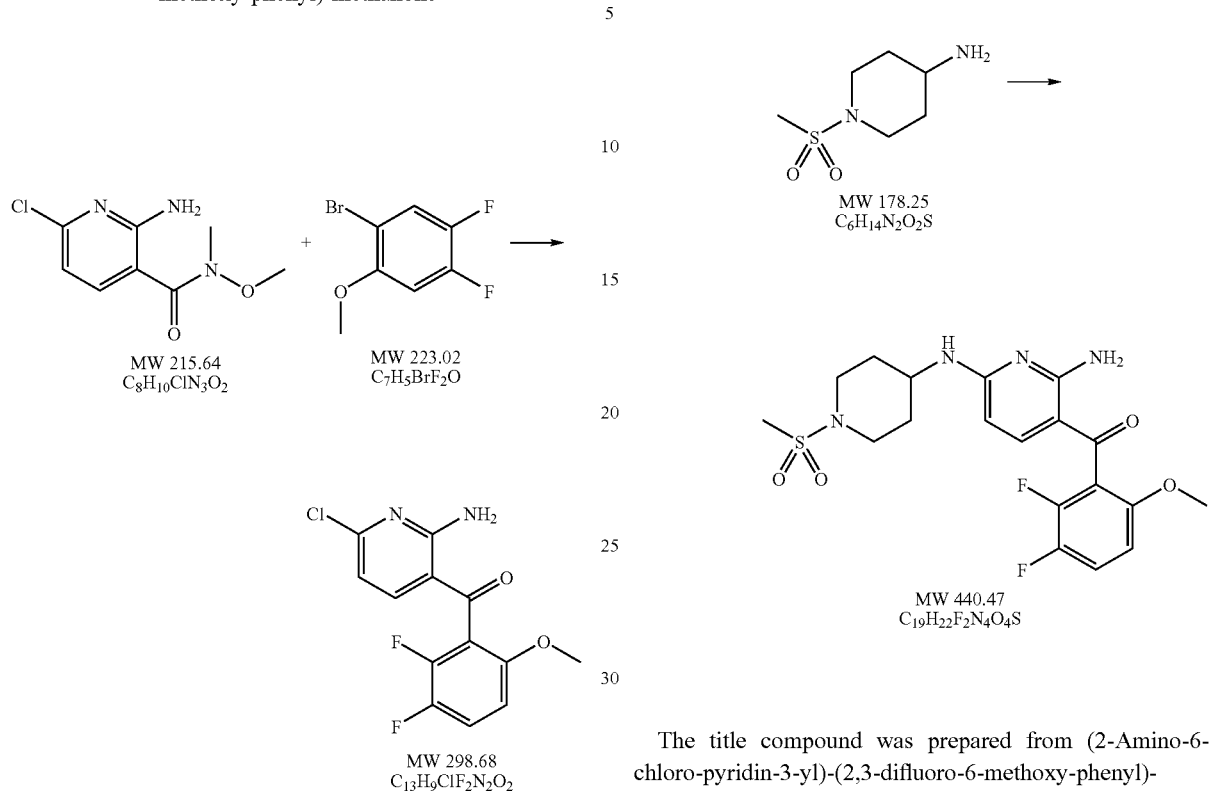

The title compound was prepared from 2-Amino-6-chloro-N-methoxy-N-methyl-nicotinamide (Example 3) and 2-bromo-4,5-difluoroanisole (Apollo) using the procedure described in Example 7. HRMS, observed: 298.0318, Calcd for M+: 298.0321.

Example 40

[2-Amino-6-(1-methanesulfonyl-piperidin-4-ylamino)-pyridin-3-yl]-(2,3-difluoro-6-methoxy-phenyl)-methanone

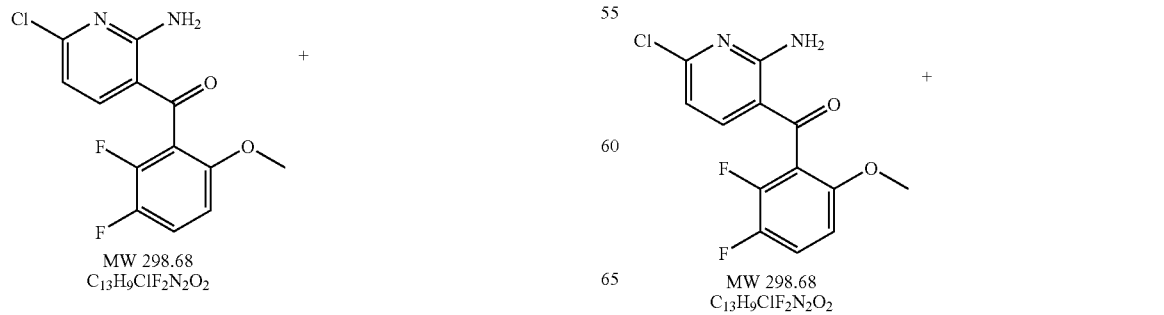

The title compound was prepared from (2-Amino-6-chloro-pyridin-3-yl)-(2,3-difluoro-6-methoxy-phenyl)-methanone (Example 39) and 1-methanesulfonyl-piperidin-4-ylamine (Step A. Example 6) using the procedure described in Step B. Example 6. HRMS, observed: 441.1407, Calcd for (M+H)+: 441.1403. $K_i$ for cdk4=0.017 μM, cdk1=0.060 μM, cdk2=0.054 and $IC_{50}$ for HCT116 cell line=2.6 μM.

Example 41

4-[6-Amino-5-(2,3-difluoro-6-methoxy-benzoyl)-pyridin-2-ylamino]-piperidine-1-carboxylic acid ethyl ester

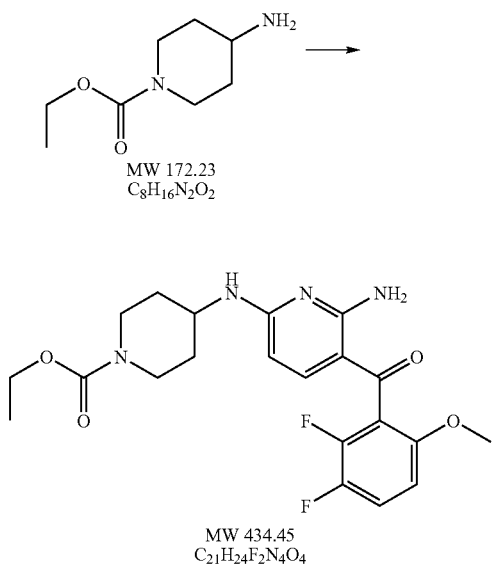

The title compound was prepared from (2-Amino-6-chloro-pyridin-3-yl)-(2,3-difluoro-6-methoxy-phenyl)-methanone (Example 39) and ethyl 4-amino-1-piperidine carboxylate (Aldrich 96%) using the procedure described in Step B. Example 6. HRMS, observed: 435.1841, Calcd for (M+H)⁺: 435.1839.

Example 42

1-{4-[6-Amino-5-(2,3-difluoro-6-methoxy-benzoyl)-pyridin-2-ylamino]-piperidin-1-yl}-ethanone

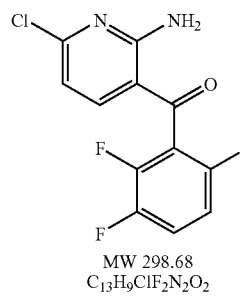

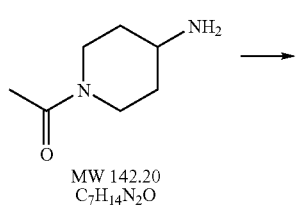

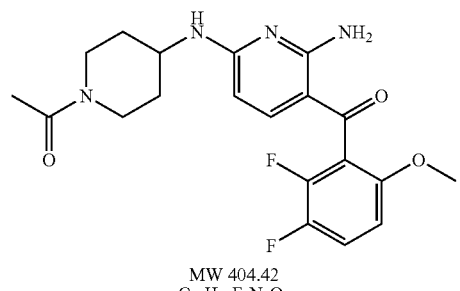

The title compound was prepared from (2-Amino-6-chloro-pyridin-3-yl)-(2,3-difluoro-6-methoxy-phenyl)-methanone (Example 39) and 1-(4-amino-piperidin-1-yl)-ethanone (prepared as described in Manetti et al, *Biorg. Med. Chem. Lett.*, 13 (2003), 2303-2306) using the procedure described in Step B. Example 6. HRMS, observed: 405.1734, Calcd for (M+H)⁺: 405.1733.

Example 43

(2-Amino-6-chloro-pyridin-3-yl)-(5-fluoro-2-methoxy-4-methyl-phenyl)-methanone

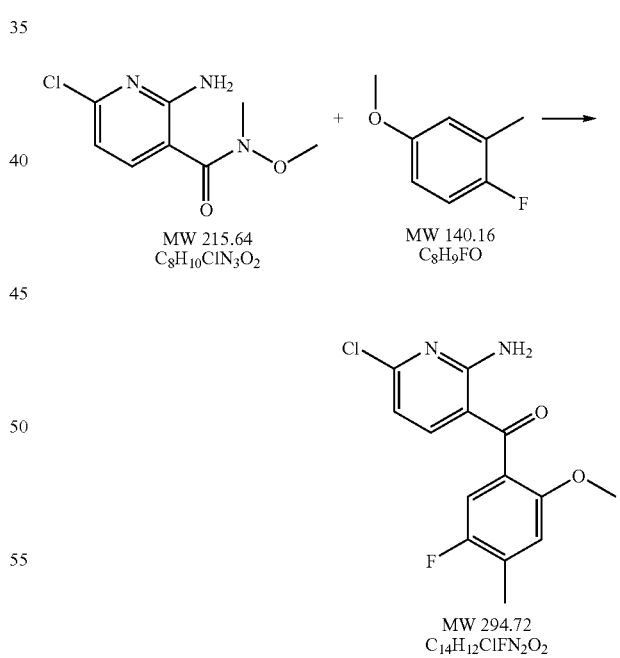

To a solution of 4-fluoro-3-methylanisole (0.75 mL, 802 mg, 5.55 mmol, Aldrich 97%) in anhydrous tetrahydrofuran (5 mL) at −78° C., was added slowly a solution of n-butyllithium in hexanes (2.5 M, 2.22 mL, 5.55 mmol, Aldrich). The reaction was stirred at −78° C. for 10 mins before it was allowed to warm to −25-0° C. and stirred for 1.5 hour. The resulting aryllithium reagent was cooled back to −78° C. and reacted with 2-Amino-6-chloro-N-methoxy-N-methyl-nicotinamide as described in Example 7 to give (2-Amino-6-chloro-pyridin-3-yl)-(5-fluoro-2-methoxy-4-methyl-phenyl)-methanone as an off-white solid. HRMS, observed: 295.0645, Calcd for (M+H)$^+$: 295.0644.

Example 44

1-{4-[6-Amino-5-(5-fluoro-2-methoxy-4-methyl-benzoyl)-pyridin-2-ylamino]-piperidin-1-yl}-ethanone

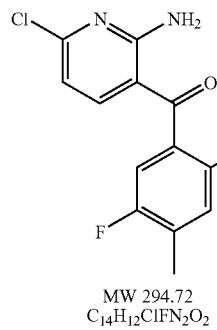

MW 294.72
$C_{14}H_{12}ClFN_2O_2$

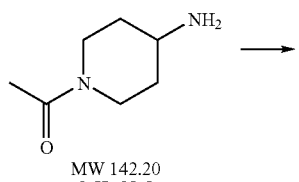

MW 142.20
$C_7H_{14}N_2O$

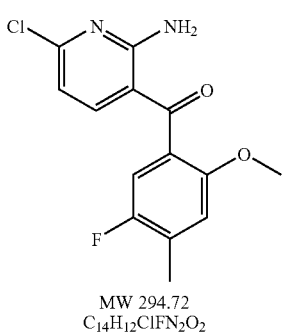

MW 400.46
$C_{21}H_{25}FN_4O_3$

The title compound was prepared from (2-Amino-6-chloro-pyridin-3-yl)-(5-fluoro-2-methoxy-4-methyl-phenyl)-methanone (Example 43) and 1-(4-amino-piperidin-1-yl)-ethanone (prepared as described in D. Manefti et al, *Biorg. Med. Chem. Lett.*, 13 (2003), 2303-2306) using the procedure described in Step B. Example 6. HRMS, observed: 401.1084, Calcd for (M+H)$^+$: 401.1084.

Example 45

[2-Amino-6-(1-methanesulfonyl-piperidin-4-ylamino)-pyridin-3-yl]-(5-fluoro-2-methoxy-4-methyl-phenyl)-methanone

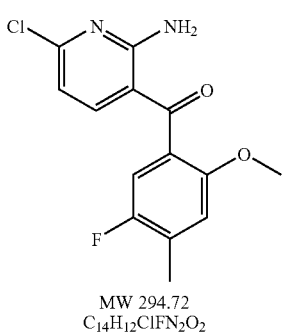

MW 294.72
$C_{14}H_{12}ClFN_2O_2$

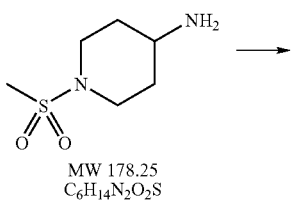

MW 178.25
$C_6H_{14}N_2O_2S$

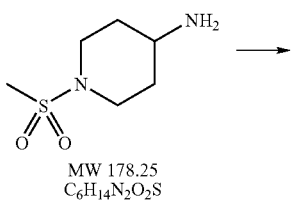

MW 436.51
$C_{20}H_{25}FN_4O_4S$

The title compound was prepared from (2-Amino-6-chloro-pyridin-3-yl)-(5-fluoro-2-methoxy-4-methyl-phenyl)-methanone (Example 43) and 1-methanesulfonyl-piperidin-4-ylamine (Step A, Example 6) using the procedure described in Step B. Example 6. HRMS, observed 437.1653, Calcd for (M+H)$^+$: 437.1654.

Example 46

4-[6-Amino-5-(5-fluoro-2-methoxy-4-methyl-benzoyl)-pyridin-2-ylamino]-piperidine-1-carboxylic acid ethyl ester

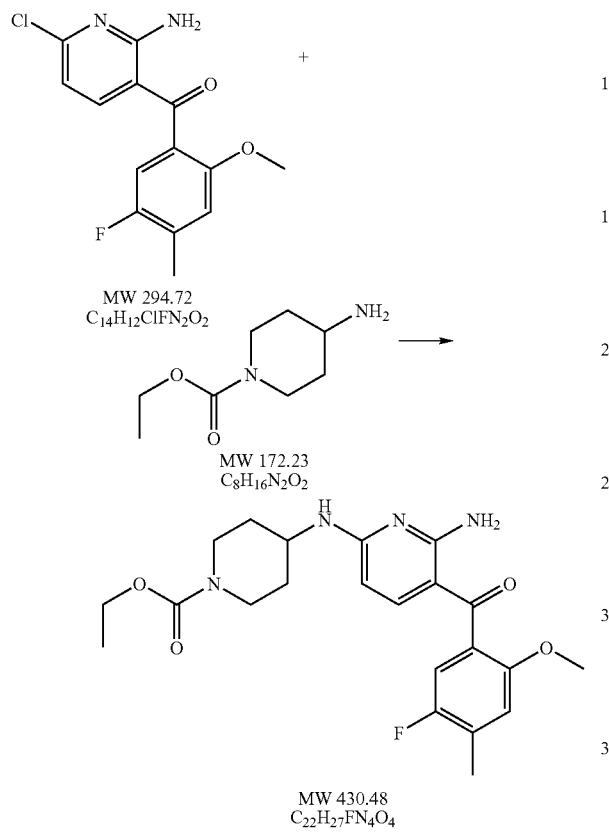

The title compound was prepared from (2-Amino-6-chloro-pyridin-3-yl)-(5-fluoro-2-methoxy-4-methyl-phenyl)-methanone (Example 43) and ethyl-4-amino-1-piperidine carboxylate (Aldrich 96%) using the procedure described in Step B. Example 6. HRMS, observed: 431.2090, Calcd for (M+H)$^+$: 431.2089.

Example 47

(2-Amino-6-chloro-pyridin-3-yl)-(4-chloro-5-fluoro-2-methoxy-phenyl)-methanone

A. 5-Chloro-4-fluoro-2-iodoanisole

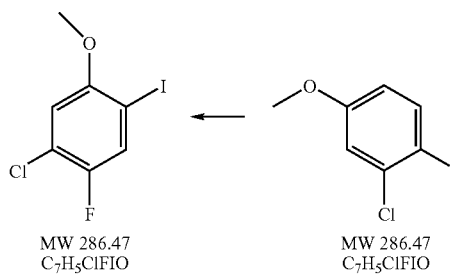

To a solution of 3-chloro-4-fluoroanisole (4.69 g, Lancaster) in chloroform (250 mL) was added silver trifluoroacetate (23.2 g, Aldrich) followed by iodine (15.8 g, Aldrich) in several portions. The reaction mixture was stirred for 2 hours and filtered through Celite. The filtrate was washed with water, brine, dried and concentrated. The crude product was purified by crystallization from ether/petroleum ether to give 5-chloro-4-fluoro-2-iodoanisole (5.0 g). MS (M+H)$^+$, 285.

B. (2-Amino-6-chloro-pyridin-3-yl)-(4-chloro-5-fluoro-2-methoxy-phenyl)-methanone

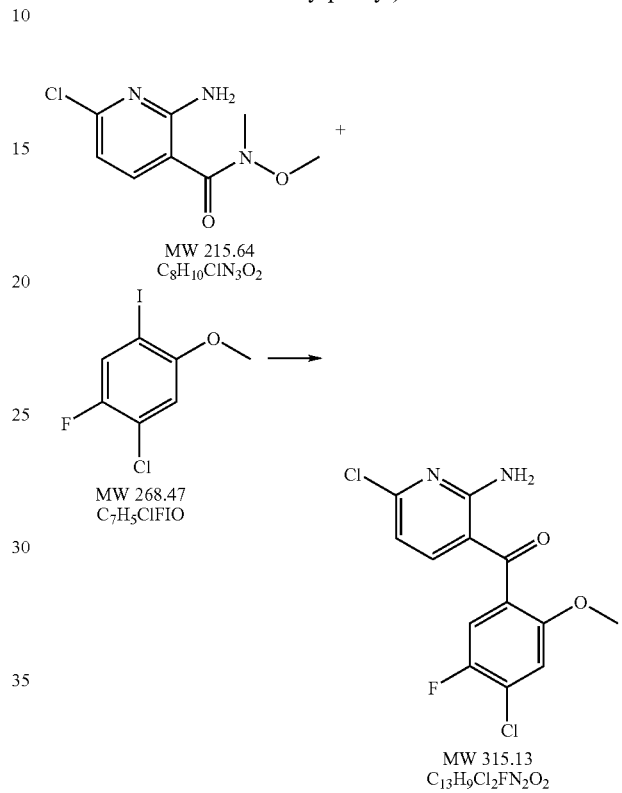

The title compound was prepared from 2-Amino-6-chloro-N-methoxy-N-methyl-nicotinamide (Example 3) and 5-chloro-4-fluoro-2-iodoanisole (prepared as described in Step A above) using the procedure described in Example 7. HRMS, observed: 312.9943, Calcd for (M−H)$^+$: 312.9947.

Example 48

1-4-[6-Amino-5-(4-chloro-5-fluoro-2-methoxy-benzoyl)-pyridin-2-ylamino]-piperidin-1-yl}-ethanone

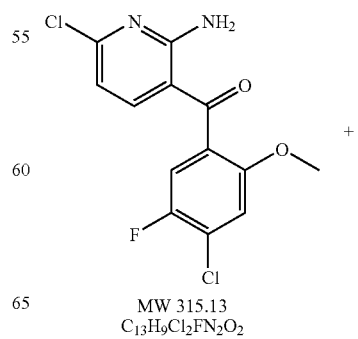

-continued

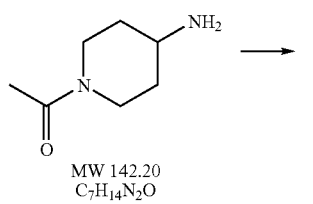

MW 142.20
C₇H₁₄N₂O

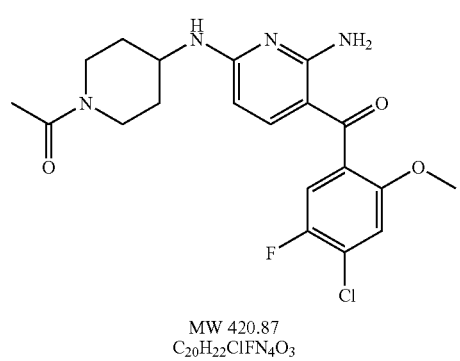

MW 420.87
C₂₀H₂₂ClFN₄O₃

The title compound was prepared from (2-Amino-6-chloro-pyridin-3-yl)-(4-chloro-5-fluoro-2-methoxy-phenyl)-methanone (Exam pie 47) and 1-(4-amino-piperidin-1-yl)-ethanone (prepared as described in D. Manefti et al, *Biorg. Med. Chem. Lett.*, 13 (2003), 2303-2306) using the procedure described in Step B. Example 6. HRMS, observed: 421.1439, Calcd for (M+H)⁺: 421.1437.

Example 49

[2-Amino-6-(1-methanesulfonyl-piperidin-4-ylamino)-pyridin-3-yl]-(4-chloro-5-fluoro-2-methoxy-phenyl)-methanone

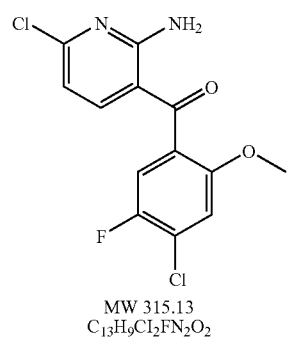

MW 315.13
C₁₃H₉Cl₂FN₂O₂

-continued

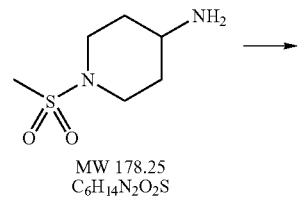

MW 178.25
C₆H₁₄N₂O₂S

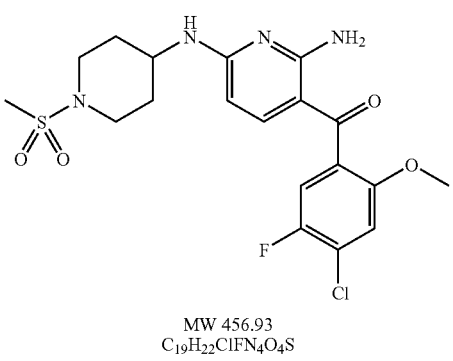

MW 456.93
C₁₉H₂₂ClFN₄O₄S

The title compound was prepared from (2-Amino-6-chloro-pyridin-3-yl)-(4-chloro-5-fluoro-2-methoxy-phenyl)-methanone (Example 47) and 1-methanesulfonyl-piperidin-4-ylamine (Step A, Example 6) using the procedure described in Step B. Example 6. HRMS, observed: 457.1106, Calcd for (M+H)⁺: 457.1107. $K_i$ for cdk4=0.008 μM, cdk1=0.154 μM, cdk2=0.039 μM, and IC50 for HCT116 cell line=3.0 μM.

Example 50

4-[6-Amino-5-(5-fluoro-2-methoxy-4-chloro-benzoyl)-pyridin-2-ylamino]-piperidine-1-carboxylic acid ethyl ester

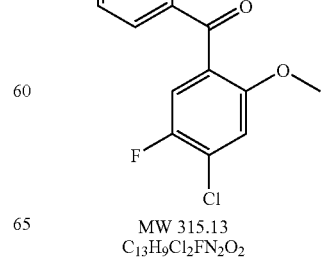

MW 315.13
C₁₃H₉Cl₂FN₂O₂

55

-continued

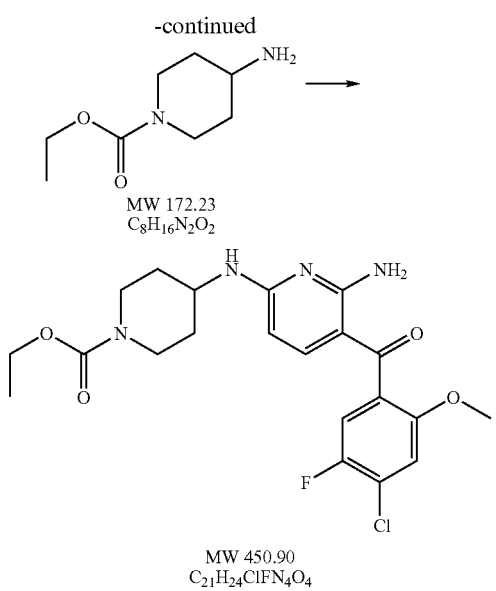

The title compound was prepared from (2-Amino-6-chloro-pyridin-3-yl)-(4-chloro-5-fluoro-2-methoxy-phenyl)-methanone (Example 47) and ethyl4-amino-1-piperidine carboxylate (Aldrich 96%) using the procedure described in Step B. Example 6. HRMS, observed: 451.1545, Calcd for (M+H)$^+$: 451.1543.

Example 51

(2-Amino-6-chloro-pyridin-3-yl)-(2,6-difluoro-phenyl)-methanone

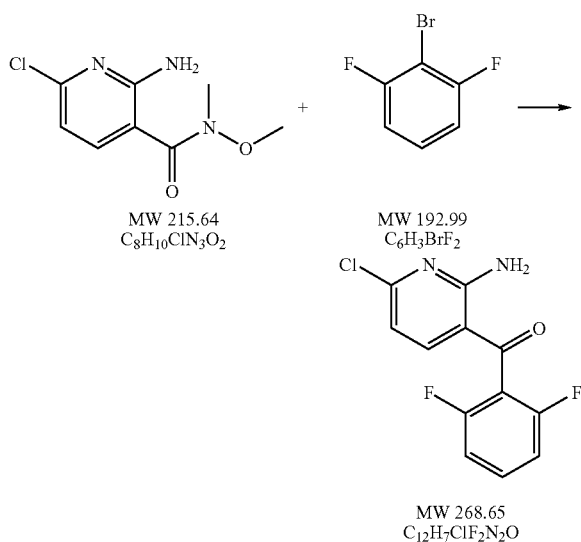

The title compound was prepared from 2-Amino-6-chloro-N-methoxy-N-methyl-nicotinamide (Example 3) and 2-bromo-1,3-difluorobenzene (Aldrich) using the procedure described in Example 7. HRMS, observed: 268.0217, Calcd for M$^+$: 268.0215.

56

Example 52

[2-Amino-6-(1-methanesulfonyl-piperidin-4-ylamino)-pyridin-3-yl]-(2,6-difluoro-phenyl)-methanone

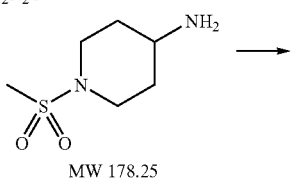

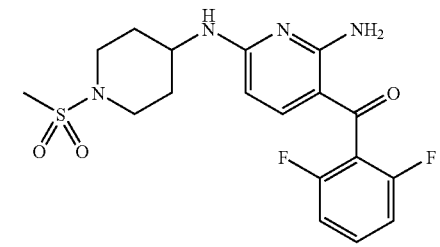

The title compound was prepared from (2-Amino-6-chloro-pyridin-3-yl)-(2,6-difluoro-phenyl)-methanone (Example 51) and 1-methanesulfonyl-piperidin-4-ylamine (Step A. Example 6) using the procedure described in Step B. Example 6. HRMS, observed: 411.1298, Calcd for (M+H)$^+$: 411.1297.

The pharmacological properties of the compounds of this invention may be confirmed by a number of pharmacological assays. The exemplified pharmacological assays which follow have been carried out with the compounds according to the invention and their salts. The compounds of the invention exhibited cdk4/cyclin D activity with Ki values of less than 3.0 µM; cdk1 and cdk2 activities with Ki values of less than 8.0 µM. Additionally, the antiproliferative potency of some compounds of the invention was tested in the human colon tumor cell line HCT116 with IC$_{50}$ values reported from an MTT assay of less than 35 µM, preferably less than 5 µM.

Example 53

Kinase Assays

Ki: Measurement

Using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. *Cell* 1993, 75, 805-816). A 6×-Histidine tagged truncated form of retinoblastoma (Rb) protein (amino acid 386-928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem.* Vol. 246 (1997) pp.581-601 and the references cited therein).

The expression of the 62Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

Using the protein constructs described above, CDK1, CDK2, and CDK4 HTRF assays were set up. These were done in 96-well format and read in 384-well plate format. The assays were run at 3× their respective Kms for ATP.

In the CDK4 assay, test compounds were diluted to 3× their final concentrations in 25 mM Hepes, pH 7.0, 6.25 mM $MgCl_2$, 1.5 mM DTT, 135 μM ATP. The DMSO concentration was no greater than 4.76%. Twenty microliters were added to the wells of a 96-well plate. The kinase reaction was initiated by the addition of 40 μl/well of a solution containing 0.185 μM Rb and 2.25 μg/ml CDK4 in 25 mM Hepes, pH 7.0, 6.25 mM $MgCl_2$, 0.003% Tween-20, 0.3 mg/ml BSA, 1.5 mM DTT. Blank wells without CDK4 were included. The plates were incubated at 37° C. for 30 minutes with shaking. The kinase reaction was terminated by the addition of 15 μl/well of 1.6 uM anti-phospho-Rb (Ser 780) antibody (Cell Signaling Inc.) in 25 mM Hepes, pH 7.0, 24 mM EDTA, 0.2 mg/ml BSA. After 30 minutes at 37° C., 15 μl/well of 3 nM Lance-Eu-W1024 labeled anti-rabbit IgG and 60 nM Allophycocyanin conjugated anti-His6 (PerkinElmer Life Sciences) in 25 mM Hepes, pH 7.0, 0.5 mg/ml BSA were added. Following a one hour incubation at 37° C., 35 μl of each well, in duplicate, were transferred to 384-well black plates. The plates were read using either ViewLux or Victor V readers (PerkinElmer Life Sciences) using an excitation wavelength of 340 nm and dual emission wavelengths of 615 nm and 665 nm. IC50 values (the concentration of test compounds reducing the assay control fluorescence read-out by 50%) were first calculated from net readings at 665nm, normalized for europium readings at 615 nm. For ATP competitive inhibitors, the Ki values were calculated according to the following equation:

$Ki=IC50/(1+S/Km)$ where S refers to the substrate concentration (ATP) and Km refers to the Michaelis-Menten constant for the ATP.

The CDK1 and CDK2 assays were similarly run except for small differences in reagent and protein concentrations:

The compound and enzyme buffers for both assays contained 10 mM $MgCl_2$. For CDK1 and CDK2, the respective reagent ATP concentrations were 162 uM and 90 uM. CDK1 at a reagent concentration of 0.15 ng/ul and CDK2 at a reagent concentration of 0.06 ng/ul were used. Reagent concentrations of detection reagents were adjusted between 3-12 nM Eu-Ab and 60-90 nM APC-antiHis 6 to give signal to background ratios of at least 10 to 1.

Example 54

Cell Based Assays (Tetrazolium dye proliferation assay)("MTT Assay")

Proliferation was evaluated by the tetrazolium dye assay according to the procedure of Denizot and Lang (Denizot, F. and Lang, R. *J Immunol Methods* 1986, 89, 271-277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5-3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100 (% INH=(1.00−$S_{AVE}$/$C_{AVE}$)×100). The concentration at which 90% inhibition of cell proliferation is obtained (the $IC_{90}$) is determined from the linear regression of a plot of the logarithm of the concentration versus percent inhibition.

Example 55

| Tablet Formulation | | | | | | | |
|---|---|---|---|---|---|---|---|
| Item | Ingredients | Mg/Tablet | | | | | |
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |

-continued

Tablet Formulation

| Item | Ingredients | Mg/Tablet | | | | | |
|---|---|---|---|---|---|---|---|
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 56

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 57

Injection Solution/Emulsion Preparation

| Item | Ingredient | mg/mL |
|---|---|---|
| 1 | Compound A * | 1 mg |
| 2 | PEG 400 | 10-50 mg |
| 3 | Lecithin | 20-50 mg |
| 4 | Soy Oil | 1-5 mg |
| 5 | Glycerol | 8-12 mg |
| 6 | Water q.s. | 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 58

Injection Solution/Emulsion Preparation

| Item | Ingredient | mg/mL |
|---|---|---|
| 1 | Compound A * | 1 mg |
| 2 | Glycofurol | 10-50 mg |
| 3 | Lecithin | 20-50 mg |
| 4 | Soy Oil | 1-5 mg |
| 5 | Glycerol | 8-12 mg |
| 6 | Water | q.s. 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

The invention claimed is:
1. A compound of the formula

$$\begin{array}{c} \text{R1-NH} \overset{6}{\underset{}{\diagup}} \overset{N}{\diagdown} \overset{2}{\underset{}{\diagdown}} \text{NH}_2 \\ \phantom{R1-NH}\underset{3}{\diagdown} \text{C(O)R2} \end{array} \quad \text{I}$$

wherein
R$^1$ is selected from the group consiting of:
 heterocycle and lower alkyl-heterocycle, wherein the heterocycle moiety in both instances optionally may be substituted by up to four substituents independently selected from the group consisting of:
  (a) H,
  (b) lower alkyl,
  (c) lower alkyl substituted by oxo, OR$^{12}$, CO$_2$R$^{12}$, NR$^5$R$^6$, S(O)$_n$R$^{15}$, aryl or C(O)NR$^5$R$^6$,
  (d) CO$_2$R$^7$,
  (e) COR$^{12}$,
  (f) C(O)NR$^{13}$R$^{14}$,
  (g) S(O)$_n$R$^{15}$,
  (h) oxo,
  (i) OR$^{12}$; or
  (j) NR$^5$R$^6$,
R$^2$ is selected from the group consisting of:
 aryl, heteroaryl, cycloalkyl and heterocycle, wherein each may be substituted by up to four substituents independently selected from the group consisting of:
  (a) lower alkyl,
  (b) lower alkyl substituted by halogen or OR$^{10}$,
  (c) halogen,
  (d) OR$^{12}$, (e) $NO_2$,
(f) CN,
(g) $NR^5R^6$,
(h) $S(O)_n$—$R^9$, and
(i) $SO_2$—$NR^{16}R^{17}$;

$R^5$ and $R^6$ are each independently selected from the group consisting of:
(a) H,
(b) lower alkyl,
(c) lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
(d) cycloalkyl,
(e) cycloalkyl substituted by $CO_2R^{12}$, $OR^{12}$, $NR^{13}R^{14}$, $C(O)NR^{13}R^{14}$ or $SO_2R^{15}$,
(f) aryl,
(g) aryl substituted by $NR^{13}R^{14}$, $OR^{12}$, $CO_2R^{12}$, $C(O)NR^{13}R^{14}$, $SO_2R^{15}$, halogen, lower alkyl, or lower alkyl substituted by halogen, $OR^{12}$, oxo, $CO_2R^{12}$, $C(O)NR^{13}R^{14}$ or $NR^{13}R^{14}$,
(h) $SO_2R^{15}$,
(i) $CO_2R^{12}$,
(j) $COR^{12}$, and
(k)

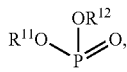

or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^{13}R^{14}$, lower alkyl and lower alkyl substituted by $OR^{12}$;

$R^7$ is selected from the group consisting of:
(a) H,
(b) lower alkyl,
(c) lower alkyl substituted by $OR^{12}$, $CO_2R^{12}$, $NR^5R^6$, or $C(O)NR^5R^6$,
(d) halogen,
(e) oxo,
(f) aryl,
(g) aryl substituted by up to three substituents independently selected from lower alkyl, halogen and $NR^5R^6$,
(h) cycloalkyl,
(i) cycloalkyl substituted by OH, oxo, or $NH_2$,
(j) $SO_2R^{15}$, and
(k) $COR^{12}$;

$R^9$ is selected from the group consisting of:
(a) H, and
(b) lower alkyl;

$R^{10}$ is selected from the group consisting of:
(a) lower alkyl,
(b) aryl, and
(c) aryl substituted by halogen or $NR^5R^6$;

$R^{11}$ is selected from the group consisting of:
(a) H,
(b) lower alkyl, and
(c) lower alkyl substituted by oxo and halogen;

$R^{12}$ is selected from the group consisting of:
(a) H,
(b) lower alkyl, and
(c) lower alkyl substituted by $NR^5R^6$ or $OR^{11}$;

$R^{13}$ and $R^{14}$ are each independently selected from the group consisting of:
(a) H,
(b) lower alkyl,
(c) lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
(d) cycloalkyl,
(e) cycloalkyl substituted by $CO_2R^{12}$, $OR^{12}$, $NR^5R^6$, $CONR^5R^6$ or $SO_2R^{15}$,
(f) aryl,
(g) aryl substituted by $NR^5R^6$, $OR^{12}$, $CO_2R^{12}$, $CONR^5R^6$, $SO_2R^{15}$, halogen, lower alkyl, and lower alkyl substituted by halogen, $OR^{12}$, oxo, $CO_2R^{12}$, $C(O)NR^5R^6$ or $NR^5R^6$;
(h) $SO_2R^{15}$,
(i) $CO_2R^{12}$,
(j) $COR^{12}$, and
(k)

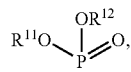

or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group consisting of:
(a) aryl,
(b) aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
(c) heteroaryl,
(d) heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
(e) $NR^5R^6$,
(f) lower alkyl,
(g) lower alkyl substituted by halogen, $OR^{12}$, oxo, $CO_2R^{12}$, $C(O)NR^5R^6$ or $NR^5R^6$,
(h) heterocycle, and
(i) heterocycle substituted by the group $CO_2R^{12}$, $COR^{12}$, $SO_2R^{12}$, lower alkyl, $C(O)NR^5R^6$ or $NR^5R^6$;

$R^{16}$ and $R^{17}$ are each independently selected from the group consisting of:
(a) H, and
(b) lower alkyl,
or, alternatively, the group —$NR^{16}R^{17}$ can form a ring having a total of from 3 to 7 ring atoms, said ring atoms comprising in addition to the nitrogen to which $R^{16}$ and $R^{17}$ are bonded, carbon ring atoms, said carbon ring atoms optionally being replaced by one or more additional N or O ring atoms, and said ring atoms optionally being substituted by lower alkyl, OH, oxo and $NH_2$; and n is 0, 1 or 2;

or the pharmaceutically acceptable salts or carboxylic acid esters thereof.

2. The compound of claim 1 wherein $R^2$ is phenyl.

3. The compound of claim 2 wherein $R^2$ is phenyl substituted by halogen or $OR^{12}$, and $R^{12}$ is lower alkyl.

4. The compound of claim 3 wherein the halogen is F and the $R^{12}$ is methyl.

5. The compound of claim 1 wherein $R^1$ is selected from the group consisting of:

(a)
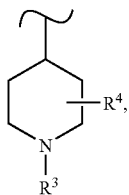

(b)
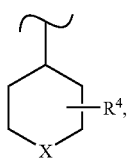

(c)
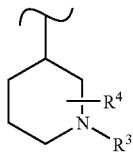

(d)
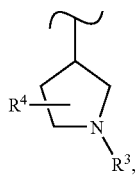

wherein $R^3$ is selected from the group consisting of:
(a) H,
(b) lower alkyl,
(c) lower alkyl substituted by oxo, $OR^{12}$, $CO_2R^{12}$, $NR^5R^6$, $SO_2R^{15}$, aryl or $C(O)NR^5R^6$,
(d) $CO_2R^7$,
(e) $COR^{12}$,
(f) $C(O)NR^5R^6$, and
(g) $SO_2R^{15}$;

$R^4$ is selected from the group consisting of:
(a) H,
(b) $OR^{11}$,
(c) lower alkyl,
(d) $NR^5R^6$,
(e) $NO_2$,
(f) oxo
(g) CN, and
(h) halogen;

$R^5$ and $R^6$ are each independently selected from the group consisting of:

(a) H,
(b) lower alkyl,
(c) lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
(d) cycloalkyl,
(e) cycloalkyl substituted by $CO_2R^{12}$, $OR^{12}$, $NR^{13}R^{14}$, $C(O)NR^{13}R^{14}$ or $SO_2R^{15}$,
(f) aryl,
(g) aryl substituted by $NR^{13}R^{14}$, $OR^{12}$, $CO_2R^{12}$, $CONR^{13}R^{14}$, $SO_2R^{15}$, halogen, lower alkyl, and lower alkyl substituted by halogen, $OR^{12}$, oxo, $CO_2R^{12}$, $CONR^{13}R^{14}$ or $NR^{13}R^{14}$;
(h) $SO_2R^{15}$,
(i) $CO_2R^{12}$,
(j) $COR^{12}$, and
(k)
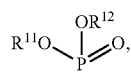

or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $N^{13}R^{14}$, lower alkyl and lower alkyl substituted by $OR^{12}$;

$R^7$ is selected from the group
(a) H,
(b) lower alkyl,
(c) lower alkyl substituted by $OR^{12}$, $CO_2R^{12}$, $NR^5R^6$, or $CONR^5R^6$,
(d) halogen,
(e) oxo,
(f) aryl,
(g) aryl substituted by up to three substituents ndependently selected from lower alkyl, halogen, or $NR^5R^6$,
(h) cycloalkyl,
(i) cycloalkyl substituted by OH, oxo, or $NH_2$, $SO_2R^{15}$, and
(j) $COR^{12}$;

$R^{10}$ is selected from the group consisting of:
(a) lower alkyl,
(b) aryl, and
(c) aryl substituted by halogen or $NR^5R^6$;

$R^{11}$ is selected from the group consisting of
(a) H,
(b) lower alkyl, and
(c) lower alkyl substituted by oxo and halogen;

$R^{12}$ is selected from the group consisting of:
(a) H
(b) lower alkyl, and
(c) lower alkyl substituted by halogen, oxo, $NR^5R^6$ or $OR^{11}$;

$R^{13}$ and $R^{14}$ are independently selected from consisting of:
(a) H,
(b) lower alkyl,
(c) lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
(d) cycloalkyl, (e) cycloalkyl substituted by $CO_2R^{12}$, $OR^{12}$, $NR^5R^6$, $C(O)NR^5R^6$ or $SO_2R^{15}$, (f) aryl, (g) aryl substituted by $NR^5R^6$, $OR^{12}$, $CO_2R^{12}$, $C(O)NR^5R^6$, $SO_2R^{15}$, halogen, lower alkyl, and lower alkyl substituted by halogen, $OR^{12}$, oxo, $CO_2R^{12}$, $C(O)NR^5R^6$ and $NR^5R^6$;

(h) $SO_2R^{15}$, (i) $CO_2R^{12}$, (j) $COR^{12}$, and (k)

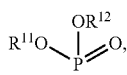

or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group consisting of:

(a) aryl, (b) aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$, (c) heteroaryl, (d) heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$, (e) $NR^5R^6$, (f) lower alkyl, (g) lower alkyl substituted by the group halogen, $OR^{12}$, oxo, $CO_2R^{12}$, $C(O)NR^5R^6$ or $NR^5R^6$, (h) heterocycle, and (i) heterocycle substituted by the group $CO_2R^{12}$, $COR^{12}$, $SO_2R^{12}$, lower alkyl, $C(O)NR^5R^6$ or $NR^5R^6$;

X is selected from the group consisting of:

(a) S, (b) SO, (c) $SO_2$, (d) O; and n is 0, 1 or 2, or the pharmaceutically acceptable salts or carboxylic acid esters thereof.

6. The compound of claim 1 wherein $R^1$ is a heterocycle that is substituted with up to four substituents independently selected from H, lower alkyl, $S(O)_nR^{15}$, $CO_2R^7$, $COR^{12}$, $C(O)NR^{13}R^{14}$.

7. The compound of claim 1 wherein $R^1$ is a heterocycle that is substituted by H, lower alkyl, $S(O)_nR^{15}$, $CO_2R^7$, $COR^{12}$, $C(O)NR^{13}R^{14}$.

8. The compound of claim 1 wherein $R^1$ is a heterocycle that is substitued by lower alkyl that is substituted by aryl.

9. The compound of claim 5 having the formula

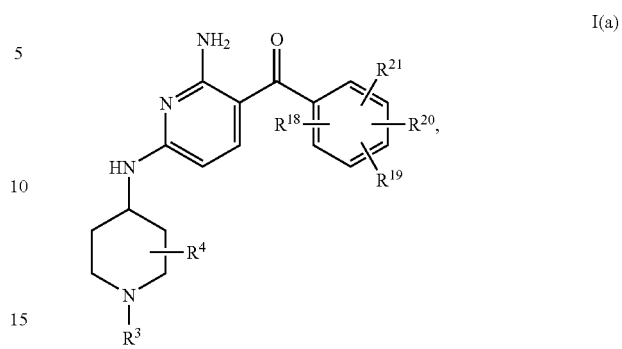

I(a)

wherein and $R^{18}$, $R^{19}$, $R^{20}$ and $R^{21}$ are each independently selected from the group consisting of lower alkyl, halogen and $OR^{12}$.

10. The compound of claim 9 wherein the halogen is F or Cl.

11. The compound of claim 9 wherein $R^3$ is selected from the group consisting of $CO_2R^7$, $COR^{12}$, $SO_2R^{15}$, $C(O)NR^5R^6$, lower alkyl and lower alkyl substituted by aryl.

12. The compound of claim 11 wherein the aryl is phenyl.

13. The compound of claim 11 wherein $R^3$ is $SO_2R^{15}$.

14. The compound of claim 13 wherein $R^{15}$ is lower alkyl or $NR^5R^6$.

15. The compound of claim 9 wherein $R^4$ is selected from H, $OR^{11}$ and lower alkyl.

16. The compound of claim 9 wherein $R^5$ and $R^6$ are each independently selected from the group consisting of H and lower alkyl, or alternatively the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms and said ring atoms optionally being substituted by OH, oxo and $NH_2$, lower alkyl or lower alkyl substituted by $OR^{12}$.

17. The compound of claim 16 wherein $R^{12}$ is lower alkyl.

18. The compound of claim 5 which is selected from the group consisting of:

[2-Amino-6-(1-methanesulfonyl-piperidin-4-ylamino)-pyridin-3-yl]-(2-methoxy-phenyl)-methanone;

[2-Amino-6-(1-methanesulfonyl-piperidin-4-ylamino)-pyridin-3-yl]-(2-fluoro-phenyl)-methanone;

4-[6-Amino-5-(2-fluoro-benzoyl)-pyridin-2-ylamino]-piperidine-1-carboxylic acid ethyl ester;

[2-Amino-6-(1-ethanesulfonyl-piperidin-4-ylamino)-pyridin-3-yl]-(2-fluoro-phenyl)-methanone;

1-{4-[6-Amino-5-(2-fluoro-benzoyl)-pyridin-2-ylamino]-piperidin-1-yl}-ethanone;

1-{4-[6-Amino-5-(2-fluoro-benzoyl)-pyridin-2-ylamino]-piperidin-1-yl}-propan-1-one;

4-[6-Amino-5-(2-fluoro-benzoyl)-pyridin-2-ylamino]-piperidine-1-carboxylic acid ethylamide;

4-[6-Amino-5-(2-fluoro-benzoyl)-pyridin-2-ylamino]-piperidine-1-carboxylic acid methylamide;

[2-Amino-6-(1-methanesulfonyl-piperidin-4-ylamino)-pyridin-3-yl]-(3-methoxy-phenyl)-methanone; and 4-[6-Amino-5-(5-fluoro-2-methoxy-benzoyl)-pyridin-2-ylamino]-piperidine-1-carboxylic acid ethyl ester.

19. The compound of claim 5 that is selected from the group consisting of:

[2-Amino-6-(1-methanesulfonyl-piperidin-4-ylamino)-pyridin-3-yl]-(5-fluoro-2-methoxy-phenyl)-methanone;

[2-Amino-6-(1-ethanesulfonyl-piperidin-4-ylamino)-pyridin-3-yl]-(5-fluoro-2-methoxy-phenyl)-methanone;

{2-Amino-6-[1-(propane-1-sulfonyl)-piperidin4-ylamino]-pyridin-3-yl}-(5-fluoro-2-methoxy-phenyl)-methanone;

{2-Amino-6-[1-(propane-2-sulfonyl)-piperidin-4-ylamino]-pyridin-3-yl}-(5-fluoro-2-methoxy-phenyl)-methanone;

4-[6-Amino-5-(5-fluoro-2-methoxy-benzoyl)-pyridin-2-ylamino]-piperidine-1-carboxylic acid methyl ester;

4-[6-Amino-5-(5-fluoro-2-methoxy-benzoyl)-pyridin-2-ylamino]-piperidine-1-carboxylic acid propyl ester;

[2-Amino-6-(1-benzyl-piperidin-4-ylamino)-pyridin-3-yl]-(5-fluoro-2-methoxy-phenyl)-methanone;

1-{4-[6-Amino-5-(5-fluoro-2-methoxy-benzoyl)-pyridin-2-ylamino]-piperidin-1-yl}-ethanone; and 1-{4-[6-Amino-5-(5-fluoro-2-methoxy-benzoyl)-pyridin-2-ylamino]-piperidin-1-yl}-propan-1-one.

20. The compound of claim 5 that is selected from the group consisting of:

4-[6-Amino-5-(5-fluoro-2-methoxy-benzoyl)-pyridin-2-ylamino]-piperidine-1-carboxylic acid methylamide;

4-[6-Amino-5-(5-fluoro-2-methoxy-benzoyl)-pyridin-2-ylamino]-piperidine-1-carboxylic acid ethylamide;

[2-Amino-6-(1-methyl-piperidin-4-ylamino)-pyridin-3-yl]-(5-fluoro-2-methoxy-phenyl)-methanone;

[2-Amino-6-(1-methanesulfonyl-piperidin-4-ylamino)-pyridin-3-yl]-(4-methoxy-phenyl)-methanone;

[2-Amino-6-(1-methanesulfonyl-piperidin-4-ylamino)-pyridin-3-yl]-(4-fluoro-phenyl)-methanone;

[2-Amino-6-(1-methanesulfonyl-piperidin-4-ylamino)-pyridin-3-yl]-(2,3-difluoro-6-methoxy-phenyl)-methanone;

4-[6-Amino-5-(2,3-difluoro-6-methoxy-benzoyl)-pyridin-2-ylamino]-piperidine-1-carboxylic acid ethyl ester;

1-{4-[6-Amino-5-(2,3-difluoro-6-methoxy-benzoyl)-pyridin-2-ylamino]-piperidin-1-yl}-ethanone; and 1-{4-[6-Amino-5-(5-fluoro-2-methoxy-4-methyl-benzoyl)-pyridin-2-ylamino]-piperidin-1-yl}-ethanone.

21. The compound of claim 5 that is selected from the group consisting of:

[2-Amino-6-(1-methanesulfonyl-piperidin-4-ylamino)-pyridin-3-yl]-(5-fluoro-2-methoxy-4-methyl-phenyl)-methanone;

4-[6-Amino-5-(5-fluoro-2-methoxy-4-methyl-benzoyl)-pyridin-2-ylamino]-piperidine-1-carboxylic acid ethyl ester;

1-{4-[6-Amino-5-(4-chloro-5-fluoro-2-methoxy-benzoyl)-pyridin-2-ylamino]-piperidin-1-yl}-ethanone;

[2-Amino-6-(1-methanesulfonyl-piperidin-4-ylamino)-pyridin-3-yl]-(4-chloro-5-fluoro-2-methoxy-phenyl)-methanone;

4-[6-Amino-5-(5-fluoro-2-methoxy-4-chloro-benzoyl)-pyridin-2-ylamino]-piperidine-1-carboxylic acid ethyl ester; and

[2-Amino-6-(1-methanesulfonyl-piperidin-4-ylamino)-pyridin-3-yl]-(2,6-difluoro-phenyl)-methanone.

22. A pharmaceutical composition comprising as an active ingredient an effective amount of a compound of claim 1 and a pharmaceutically acceptable carrier or excipient.

23. The pharmaceutical composition of claim 22 which is suitable for parenteral administration.

24. A method for treating a solid colon tumor comprising administering to a subject in need of such treatment a therapeutically effective amount of at least one compound according to claim 1.

* * * * *

UNITED STATES PATENT AND TRADEMARK OFFICE
CERTIFICATE OF CORRECTION

PATENT NO. : 7,423,051 B2
APPLICATION NO. : 11/165912
DATED : September 9, 2008
INVENTOR(S) : Bartkovitz et al.

It is certified that error appears in the above-identified patent and that said Letters Patent is hereby corrected as shown below:

Claim 5, Column 64, line 41: "substituents ndependently" should read -- substituents independently --.

Signed and Sealed this

Eleventh Day of November, 2008

JON W. DUDAS
*Director of the United States Patent and Trademark Office*